(12) United States Patent
Takiguchi

(10) Patent No.: US 7,443,290 B2
(45) Date of Patent: Oct. 28, 2008

(54) COMMUNICATION SYSTEM

(75) Inventor: Kiyoaki Takiguchi, Sony Corporation, 7-35 Kitashinagawa 6-Chome, Shingagawa-Ku, Tokyo 141-0001 (JP)

(73) Assignee: Kiyoaki Takiguchi, Kanagawa (JP)

( * ) Notice: Subject to any disclaimer, the term of this patent is extended or adjusted under 35 U.S.C. 154(b) by 299 days.

(21) Appl. No.: 10/547,064

(22) PCT Filed: Feb. 27, 2004

(86) PCT No.: PCT/JP2004/002371

§ 371 (c)(1), (2), (4) Date: Aug. 25, 2005

(87) PCT Pub. No.: WO2004/077704

PCT Pub. Date: Sep. 10, 2004

(65) Prior Publication Data
US 2006/0077616 A1   Apr. 13, 2006

(30) Foreign Application Priority Data
Feb. 27, 2003  (JP) .............................. 2003-051867

(51) Int. Cl.
G08B 1/08 (2006.01)
G08B 13/00 (2006.01)
G08B 13/14 (2006.01)

(52) U.S. Cl. .................... 340/539.1; 340/552; 340/561; 340/572.1; 340/572.7

(58) Field of Classification Search .............. 340/538.1, 340/561, 552, 567, 572.4, 539.1
See application file for complete search history.

(56) References Cited

U.S. PATENT DOCUMENTS

| 5,914,701 | A | 6/1999 | Gersheneld et al. |
| 6,147,605 | A * | 11/2000 | Vega et al. ............... 340/572.7 |
| 6,223,018 | B1 | 4/2001 | Fukumoto et al. |
| 6,275,681 | B1* | 8/2001 | Vega et al. .................. 455/41.1 |
| 6,336,031 | B1* | 1/2002 | Schyndel .................... 455/41.2 |
| 6,611,199 | B1* | 8/2003 | Geiszler et al. .......... 340/10.51 |

(Continued)

FOREIGN PATENT DOCUMENTS

BR           9608465-0           12/1998

(Continued)

Primary Examiner—Donnie L Crosland
(74) Attorney, Agent, or Firm—Frommer Lawrence & Haug LLP; William S. Frommer; Ellen Marcie Emas

(57) ABSTRACT

The apparatus enhances the degree of freedom in communication using a quasi-electrostatic field. A card device 3 (a ticket checking and collecting machine 2) side in a communication system 1, a quasi-electrostatic field according to an identification signal S5 (a notification signal S9) modulated according to identification information S4 (notification information S8) is generated from an internal electrode 8 (a side-surface electrode 7) to electrify a human body. At the ticket checking and collecting machine 2 (the card device 3), displacement of the strength of a information-transmission quasi-electrostatic field DTD which is isotropically formed in the neighborhood of the human body is detected via the side-surface electrode 7 (the internal electrode 8) and a FET 28 (a FET 37) sequentially, and based on the detection result, the identification information S4 (the notification information S8) is demodulated. Sending and receiving of information without directional restrictions in the neighborhood of the human body, freedom in communication can be enhanced.

32 Claims, 25 Drawing Sheets

U.S. PATENT DOCUMENTS 6,992,565 B1 1/2006 Giesler
2002/0153882 A1* 10/2002 Grimes et al. ............... 324/209

FOREIGN PATENT DOCUMENTS

| DE | 696 23 115 | 11/1996 |
| --- | --- | --- |
| ES | 2 180 767 | 2/1998 |
| JP | 7-170215 | 7/1995 |
| JP | 10-229357 | 8/1998 |
| JP | 11 225119 | 8/1999 |
| JP | 11-509380 | 8/1999 |
| JP | 2002 111602 | 4/2002 |
| JP | 2002 525702 | 8/2002 |
| WO | WO 96/36134 | 11/1996 |

* cited by examiner (A) FRONT DIRECTION (B) SIDE DIRECTION

COMMUNICATION SYSTEM

TECHNICAL FIELD

The present invention relates to a communication system and is preferably applicable to a communication system for sending and receiving information via an electric field, for example.

BACKGROUND ART

Conventionally, communication systems have been adapted to send and receive information using a radiation field (radio waves), for example, between mobile telephones, and send and receive information via electromagnetic induction, for example, between the coil in a data reader/writer provided on a ticket checking and, collecting machine at a station and the coil in an IC card.

Recently, there have been proposed communication systems which are provided with a human-body-side communication device fitted in contact with the skin of a human body and an equipment-side communication device in the neighborhood of the user. In these communication systems, an alternating voltage is applied to the human body via the electrode of the human-body-side communication device, and as a result, there is caused an electrostatic induction phenomenon at the electrode of the equipment-side communication device by the action of a capacitor using a human body intervening between the electrodes of the communication device on the human body side and the communication device on the equipment side as a medium. Using the electrostatic induction phenomenon, information is sent and received (see Non-patent document 1, for example).

In addition to these communication systems, there have been proposed a lot of communication systems adapted to send and receive information utilizing the electrostatic induction phenomenon caused at a receiving electrode by the action of a capacitor using a human body intervening between sending and receiving electrodes as a medium (see Patent documents 1 to 9 and Non-patent documents 2 to 5).

[Patent document 1] National Publication of International Patent Application No. 11-509380

[Patent document 2] U.S. Pat. No. 3,074,644

[Patent document 3] Japanese Patent Laid-Open No. 10-228524

[Patent document 4] Japanese Patent Laid-Open No. 10-229357

[Patent document 5] Japanese Patent Laid-Open No. 2001-308803

[Patent document 6] Japanese Patent Laid-Open No. 2000-224083

[Patent document 7] Japanese Patent Laid-Open No. 2001-223649

[Patent document 8] Japanese Patent Laid-Open No. 2001-308803

[Patent document 9] Japanese Patent Laid-Open No. 2002-9710

[Non-patent document 1] Internet <URL:http://www.mew.co.jp/press/0103/0103-7.htm>(retrieved on Jan. 20, 2003)

[Non-patent document 2] "Development of Information Communication Device with Human Body Used as Transmission Line" by Keisuke Hachisuka, Anri Nakata, Kenji Shiba, Ken Sasaki, Hiroshi Hosaka and Kiyoshi Itao (Tokyo University); Mar. 1, 2002 (Collected Papers for Academic Lectures on Micromechatronics, Vol., 2002, Spring, pp. 27-28)

[Non-patent document 3] "Development of Communication System within Organism" by Anri Nakata; Keisuke Hachisuka, Kenji Shiba, Ken Sasaki, Hiroshi Hosaka and Kiyoshi Itao (Tokyo University); 2002 (Collected Papers for Academic Lectures for Japan Society of Precision Engineering Conference, Spring, p. 640)

[Non-patent document 4] "Review on Modeling of Communication System Utilizing Human Body as Transmission Line" by Katsuyuki Fujii (Chiba University), Koichi Date (Chiba University), Shigeru Tajima (Sony Computer Science Laboratories, Inc.); Mar. 1, 2002 (Technical Reports by The Institute of Image Information and Television Engineers Vol. 26, No. 20, pp. 13-18)

[Non-patent document 5] "Development of Information Communication Device with Human Body Used as Transmission Line" by Keisuke Hachisuka, Anri Nakata, Kento Takeda, Ken Sasaki, Hiroshi Hosaka, Kiyoshi Itao (Graduate School of Science of New Region Creation, Tokyo University) and Kenji Shiba (Science and Engineering Course, Tokyo University of Science); Mar. 18, 2002 (Micromechatronics Vol. 46; No. 2; pp. 53-64)

In these communication systems with such a configuration, since the action of a capacitor using a human body intervening between sending and receiving electrodes as a medium is the premise of physical action, the communication strength in communication between the electrodes depends on the area of the electrodes.

Furthermore, since the action of a capacitor using a human body intervening between sending and receiving electrodes as a medium is the premise of physical action, it is physically impossible, when the sending electrode is fitted to the human's right wrist, for example, to communicate in directions other than the direction from the human's right wrist to the fingertip. When the sending electrode is fitted near the human's chest, communication in directions other than the forward direction from the human's chest is physically impossible.

As described above, in communication systems, since the action of a capacitor using a human body intervening between sending and receiving electrodes as a medium is the premise of physical action, there have been a problem that the communication direction is restricted by the position of the electrode fitted to a human body-as well as a problem that the degree of freedom in communication is low because the communication strength depends on the electrode area.

DISCLOSURE OF THE INVENTION

The present invention has been made in consideration of the above problems and proposes a communication system, a communication device and a communication method capable of enhancing the degree of freedom in communication.

In the present invention, in order to solve the above problems, a communication system is configured with a first communication device for electrifying an electrification target having electrification properties by generating a quasi-electrostatic field modulated according to information to be sent; and a second communication device for detecting change in the electrification condition of the electrification target and demodulating the information based on the change.

In this case, in the communication system, it is possible to cause an electrification target to act as an antenna in a quasi-electrostatic field, isotropically from the surface of the electrification target, by electrifying the electrification target according to particular information. Therefore, it is possible to perform communication without the communication direction being restricted by the position of the electrode of the first communication device and without the communication strength depending on the electrode area, and thereby the degree of freedom in communication can be enhanced.

In the present invention, even when the electrification target is a human body, it is possible to cause the human body to act as an antenna in a quasi-electrostatic field, isotropically from the surface of the human body, irrespective of the presence or absence of movement of the human body because the human body is well electrified due to the nature thereof.

Furthermore, in the present invention, by forming an electrode with a structure according to the reference frequency such that the strength of the induction field component of the electric field is below the noise floor specified according to communication bands, energy required for communication can be reduced by reduction of the induction field component and the radiation field component unnecessary for quasi-electrostatic field communication, and unnecessary propagation can be prevented to enhance spatial resolution, which enables stabilization of communication. Thus, communication can be stabilized.

As described above, according to the present invention, an electrification target having electrification properties is electrified by generating a quasi-electrostatic field modulated according to information to be sent, and information is demodulated based on change in the electrification condition of the electrification target, so that it is possible to cause the electrification target to act as an antenna in a quasi-electrostatic field, isotropically from the surface of the electrification target, by electrification of the electrification target according to particular information. Therefore, it is possible to perform communication without the communication direction being restricted by the position of the sending-side electrode and without the communication strength depending on the electrode area, and thereby the degree of freedom in communication can be enhanced.

Furthermore, according to the present invention, even when the electrification target is a human body, it is possible to cause the human body to act as an antenna in a quasi-electrostatic field, isotropically from the surface of the human body, irrespective of the presence or absence of movement of the human body because the human body is well electrified due to the nature thereof. Thus, the degree of freedom in communication can be enhanced.

Furthermore, according to the present invention, by forming the electrode with a structure according to the reference frequency such that the strength of the induction field component of the electric field is below the noise floor specified according to communication bands, energy required for communication can be reduced by reduction of the induction field component and the radiation field component unnecessary for quasi-electrostatic field communication, and unnecessary propagation can be prevented to enhance spatial resolution, which enables stabilization of communication. Thus, communication can be stabilized and the degree of freedom in communication can be enhanced.

BEST MODE FOR CARRYING OUT THE INVENTION

Figure 1:
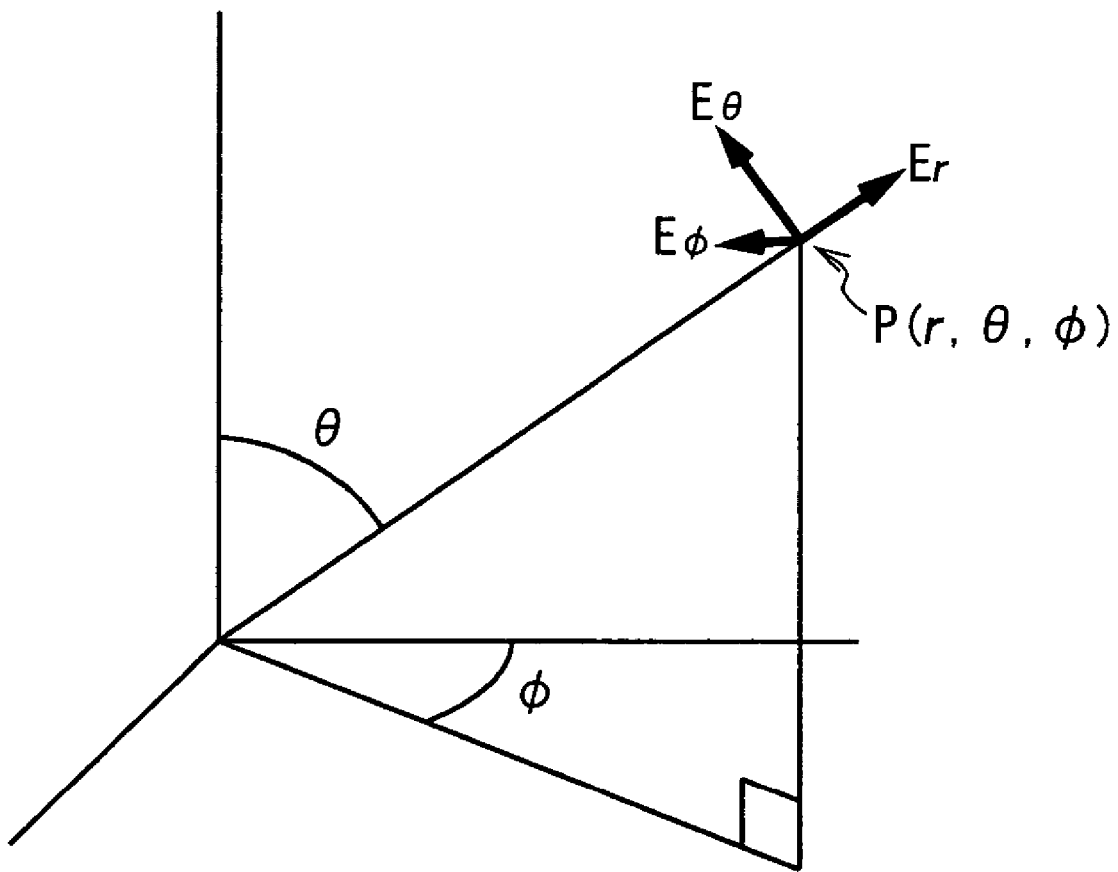
FIG. 1 is a schematic diagram provided to explain a polar coordinate system.

The present invention is now described in detail with reference to the drawings.

(1) Summary of the Invention

According to the invention, information is sent and received using an electric field. The summary of the present invention is now described in terms of the relation with the electric field.

(1-1) Electric Field

Generally, when current flows through an electric dipole (dipole antenna), the electric field E generated according to the distance r from the antenna can be represented in a simplified formula as shown below:

$$E_0 = A\left(\frac{1}{r^3} + \frac{jk}{r^2} + \frac{k^2}{r^1}\right) \quad (1)$$

where A is a constant, j is the imaginary unit, and k is the number of waves.

As shown in the above formula (1), the electric field E can be roughly separated into a component which is in inverse proportion to the distance r raised to the third power (hereinafter, this component is referred to as a quasi-electrostatic field), a component which is in inverse proportion to the distance r raised to the second power (hereinafter, this component is referred to as an induction field) and a component which is linearly in inverse proportion to the distance r (hereinafter, this component is referred to as a radiation field).

The radiation field is a component excellent in propagation capability, which does not rapidly attenuate even when the distance r is long, since it is only linearly in inverse proportion to the distance r, and therefore, it has been used as a common information transmission medium in the art of information communication.

Though the induction field is a component with little transmission capability, which attenuates in inverse proportion to the distance r raised to the second power as the distance r lengthens, it has recently been used as an information transmission medium in a part of the art of information of communication.

The quasi-electrostatic field is a component which rapidly attenuates in inverse proportion to the distance r raised to the third power and therefore does not a transmission capability and which appears in close proximity to an oscillation source only as oscillation. Therefore, it has not been utilized in the art of information communication where the radiation field and the induction field are premises.

The present invention is adapted to send and receive information within a neighbor communication range, with a neighbor communication (hereinafter referred to as near field communication) approach using a quasi-electrostatic field among electric fields.

(1-2) Quasi-Electrostatic Field

The quasi-electrostatic field is now described in more detail. First, the electric field E shown in the above formula. (1) is represented as an electric field at a position P (r, θ, φ) at a predetermined distance from the origin as described in FIG. 1.

In this case, if it is assumed that a charge q and a charge −q exist separated by a distance δ and the charge q changes to "Q cos ωt" at a time t, then the electric fields Er, Eθ and Eφ at the position P (r, θ, φ) can be represented as the following formulas, respectively, with the position of the charge q as the origin:

$$E_r = \frac{Q\cos\omega t\ \sigma\cos\theta}{2\pi\varepsilon r^3}(1 + jkr)\exp(-jkr) \quad (2)$$

$$E_\theta = \frac{Q\cos\omega t\ \sigma\sin\theta}{4\pi\varepsilon r^3}(1 + jkr + (jkr)^2)\exp(-jkr)$$

$$E_\phi = 0$$

In the formulas (2), the electric field Eφ is "zero", and this means that there is not generated any electric field in the φ direction from the position P (FIG. 1).

If the component which is linearly in inverse proportion to the distance r (that is, the radiation field) is separated from the electric fields Er and Eθ represented in the formulas (2), then the radiation field E1r and E1θ at the position P (r, θ, φ) are represented as the following formulas:

$$E_{1r} = 0 \quad (3)$$

$$E_{1\theta} = \frac{Q\cos\omega t\ \sigma\sin\theta}{4\pi\varepsilon r}(jk)^2\exp(-jkr)$$

If the component which is in inverse proportion to the distance r raised to the second power (that is, the induction field) is separated from the electric fields Er and Eθ represented in the formulas (2), then the induction fields E2r and E2θ at the position P (r, θ, φ) are represented as the following formulas:

$$E_{2r} = \frac{Q\cos\omega t\ \sigma\cos\theta}{2\pi\varepsilon r^2}jk\cdot\exp(-jkr) \quad (4)$$

$$E_{2\theta} = \frac{Q\cos\omega t\ \sigma\sin\theta}{4\pi\varepsilon r^2}jk\cdot\exp(-jkr)$$

Furthermore, if the component which is in inverse proportion to the distance r raised to the third power (that is, the quasi-electrostatic field) is separated from the electric fields Er and Eθ represented in the formulas (2), then the quasi-electrostatic fields E3r and E3θ at the position P (r, θ, φ) are represented as the following formulas:

$$E_{3r} = \frac{Q\cos\omega t\ \sigma\cos\theta}{2\pi\varepsilon r^3} \quad (5)$$

$$E_{3\theta} = \frac{Q\cos\omega t\ \sigma\sin\theta}{4\pi\varepsilon r^3}$$

In the formulas (3), only the radiation field E1r is "zero", and this means that there is not generated any radiation field in the tangent direction from the position P (FIG. 1).

Now, in order to show the component's electric field strength of each of the radiation field, the induction field and the quasi-electrostatic field at a distance r, the radiation field E1θ, the induction field E2θ and the quasi-electrostatic field E3θ in the formulas (3) to (5) are now described in more detail.

The number of waves k [m$^{-1}$] is in the relation shown as the following formula, where the angular frequency is denoted by X and the light velocity is denoted by c:

$$k = \frac{\omega}{c} \quad (6)$$

If the number of waves k is substituted into the formula (6), the "j·exp(–jkr)" is removed since it is beyond the discussion here, and the "cos ωt" is assumed to be one (1) since the maximum change with time between the charge q and the charge –q is to be considered, then the following formulas are obtained:

Radiation field (7)

$$E_{t\theta} = \frac{Q\sigma\sin\theta}{4\pi\varepsilon r^3}\left(\frac{\omega}{c}r\right)^2$$

Induction field $$E_{2\theta} = \frac{Q\sigma\sin\theta}{4\pi\varepsilon r^3}\frac{\omega}{c}r$$

Quasi-electrostatic field $$E_{3\theta} = \frac{Q\sigma\sin\theta}{4\pi\varepsilon r^3}$$

If the formulas (7) are rearranged by substituting the distance δ, the charge q(=Q) and the θ with one (1), 0.001 [C] and π/2, respectively, then the following formulas are obtained:

Radiation field (8)

$$E_{t\theta} = \frac{0.001}{4\pi\varepsilon_0 r}\left(\frac{\omega}{c}\right)^2$$

Induction field $$E_{2\theta} = \frac{0.001}{4\pi\varepsilon_0 r^2}\frac{\omega}{c}$$

Quasi-electrostatic field $$E_{3\theta} = \frac{0.001}{4\pi\varepsilon_0 r^3}$$

Figure 2:
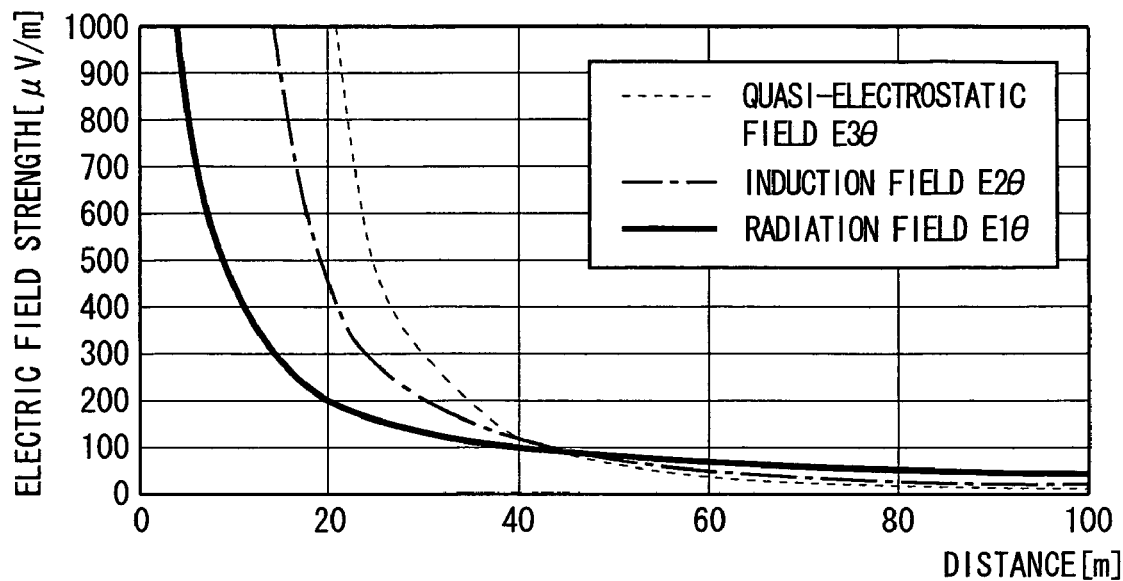
FIG. 2 is a graph showing relative strength change (1) of each electric field relative to the distance.
Figure 3:
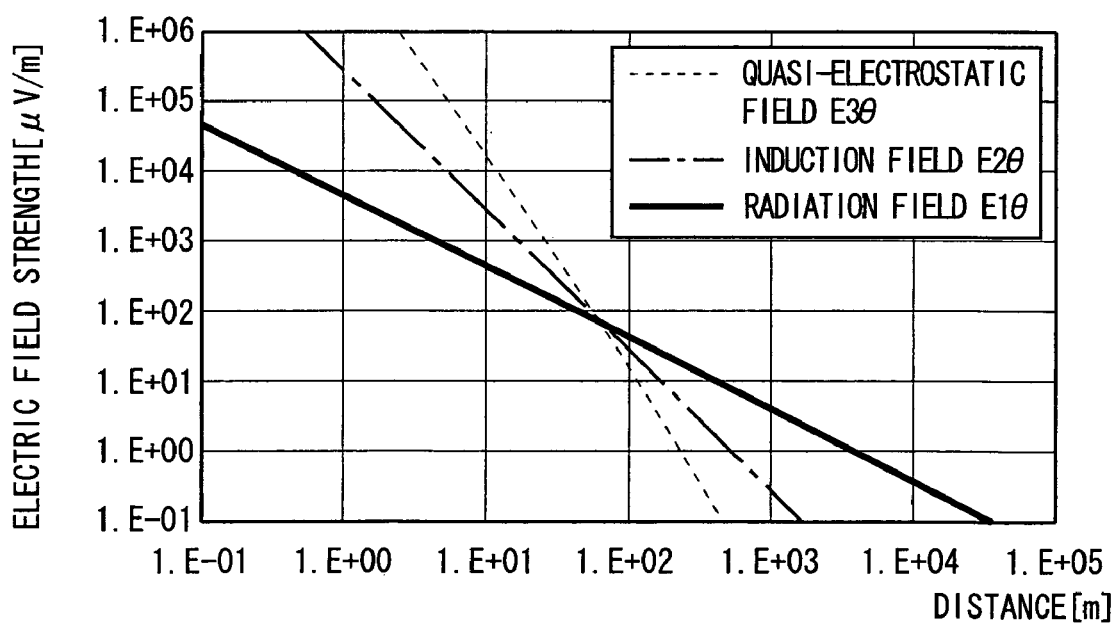
FIG. 3 is a graph showing relative strength change (2) of each electric field relative to the distance.

FIGS. 2 and 3 shows the results obtained by qualitatively plotting the component's electric field strengths of the radiation field E1θ, the induction field E2θ and the quasi-electrostatic field E3θ based on the formulas (8).

However, in FIGS. 2 and 3, the component's electric field strengths at a frequency of 1 [MHz] are shown, and in FIG. 3, the component's electric field strengths shown in FIG. 2 are substituted with indexes (index scale).

Especially apparent from FIG. 3, the component electric field strengths of the radiation field E1θ, the induction field E2θ and the quasi-electrostatic field E3θ are equal at a certain distance r (hereinafter referred to as a boundary point), and the radiation field E1θ is dominant in the distance from the boundary point. On the contrary, in the neighbor before the boundary point, the quasi-electrostatic field E3θ is dominant.

At the boundary point, the following formula is established according to the above formulas (8):

$$\frac{\omega}{c}\cdot r = 1 \quad (9)$$

The light velocity c is in the relation shown by the following formula, where the wavelength is denoted by λ and the frequency is denoted by f:

$$c = \lambda \cdot f \quad (10)$$

The angular frequency ω is in the relation shown by the following formula:

$$\omega = 2\pi f \quad (11)$$

Then, by substituting the formula (10) and the formula (11) into the formula (9) and rearranging the formula (9), the following formula is obtained:

$$r = \frac{\lambda}{2\pi} \quad (12)$$

Figure 4:
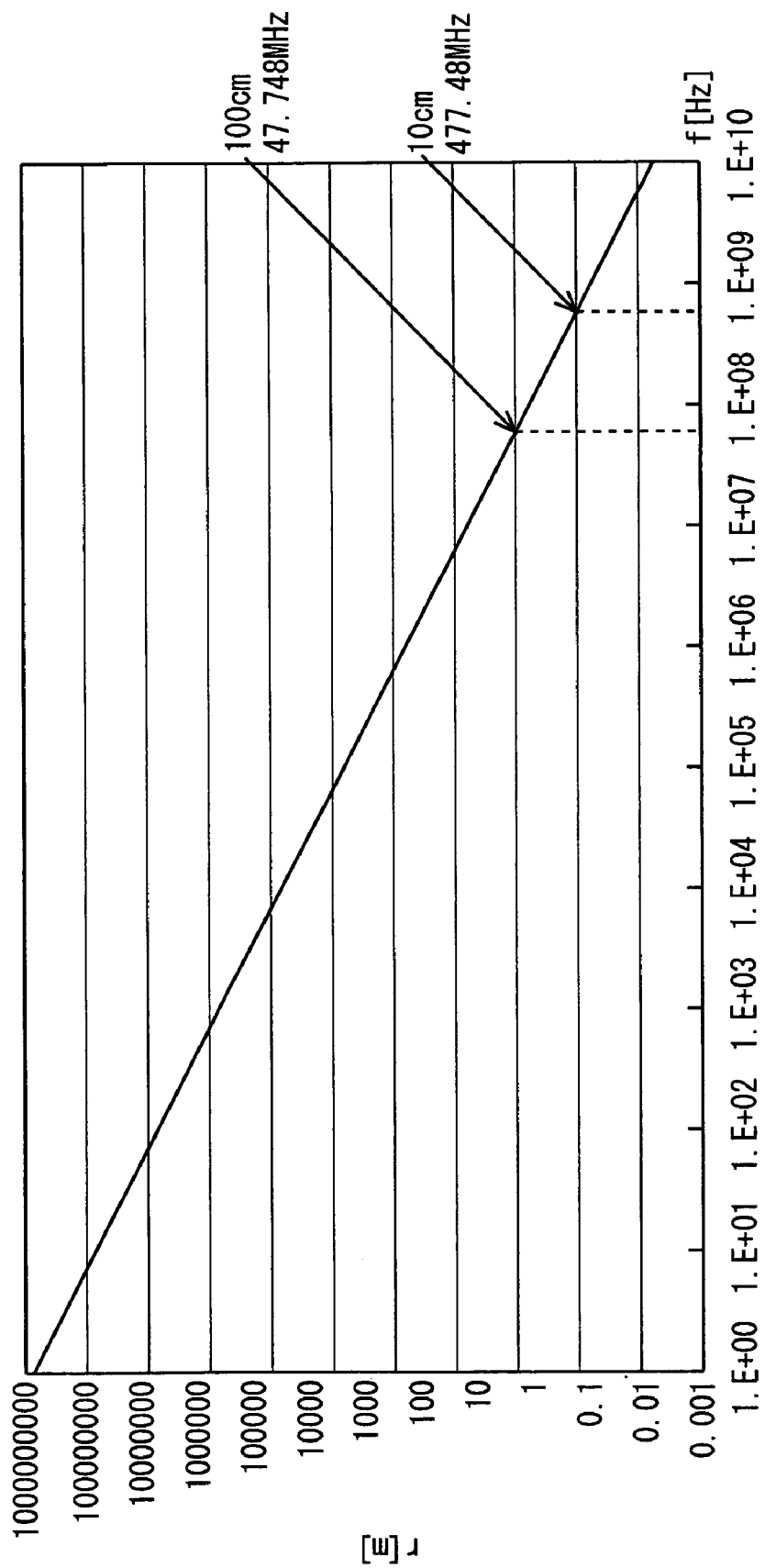
FIG. 4 is a graph showing the relation between the wavelength and the distance.

According to the formula (12), the distance r from the origin to the boundary point varies according to the wavelength λ. As shown in FIG. 4, the longer the wavelength λ is, the wider the range (the distance r from the origin to the boundary point) where the quasi-electrostatic field E3θ is dominant.

To sum up the above description, the quasi-electrostatic field E3θ is dominant within the range where the distance r from the origin is "r<λ/2π", if the relative permittivity of the air ε is assumed to be 1 and the wavelength in the air is assumed to be λ.

In the present invention, by selecting the range satisfying the formula (12) when sending and receiving information with the near field communication approach, the information is sent and received in the space where the quasi-electrostatic field E3θ is dominant.

(1-3) A Quasi-Electrostatic Field and a Human Body

Though it is necessary to apply current to a human body to cause the human body to generate a radiation field or an induction field, it is physically difficult to efficiently apply current to the human body because the impedance of a human body is very high. It is also physiologically undesirable to apply current to a human body. As for static electricity, however, the situation is completely different.

That is, a human body is very often electrified as suggested by the empirical fact that static electricity is felt in our everyday life. As it is known that a quasi-electrostatic field is generated by electrification of the surface of a human body in response to the movement of the human body, it is not necessary to apply electricity to a human body to cause the human body to generate a quasi-electrostatic field but it is only necessary to electrify the human body.

That is, a human body is electrified by extremely little movement of charge (current); the electrification change is instantaneously conducted around the surface of the human body; and then an equipotential surface of a quasi-electrostatic field is formed substantially isotropically from the periphery. Furthermore, within the range satisfying the above formula (12) where the quasi-electrostatic field is dominant, the radiation field and the induction field does not have much influence. Consequently, the human body functions efficiently as an antenna. This has already been confirmed from the results of the experiments by the applicant.

As a near field communication technology, the present information is adapted to modulate a quasi-electrostatic field which is isotropically formed in the neighborhood of a human body by electrifying the human body according to particular information, and as a result, form a quasi-electrostatic field having information in the neighborhood of the human body, through which the information is sent and received.

To sum up the present invention, as described above, it utilizes the nature of a quasi-electrostatic field and the nature of a human body; by electrifying the human body within a range where the quasi-electrostatic field is dominant, the human body is caused to act as an antenna; and the quasi-electrostatic field consequently formed in the neighborhood of the human body is used as an information transmission medium. An embodiment to which the present invention is applied is now described below.

Figure 5:
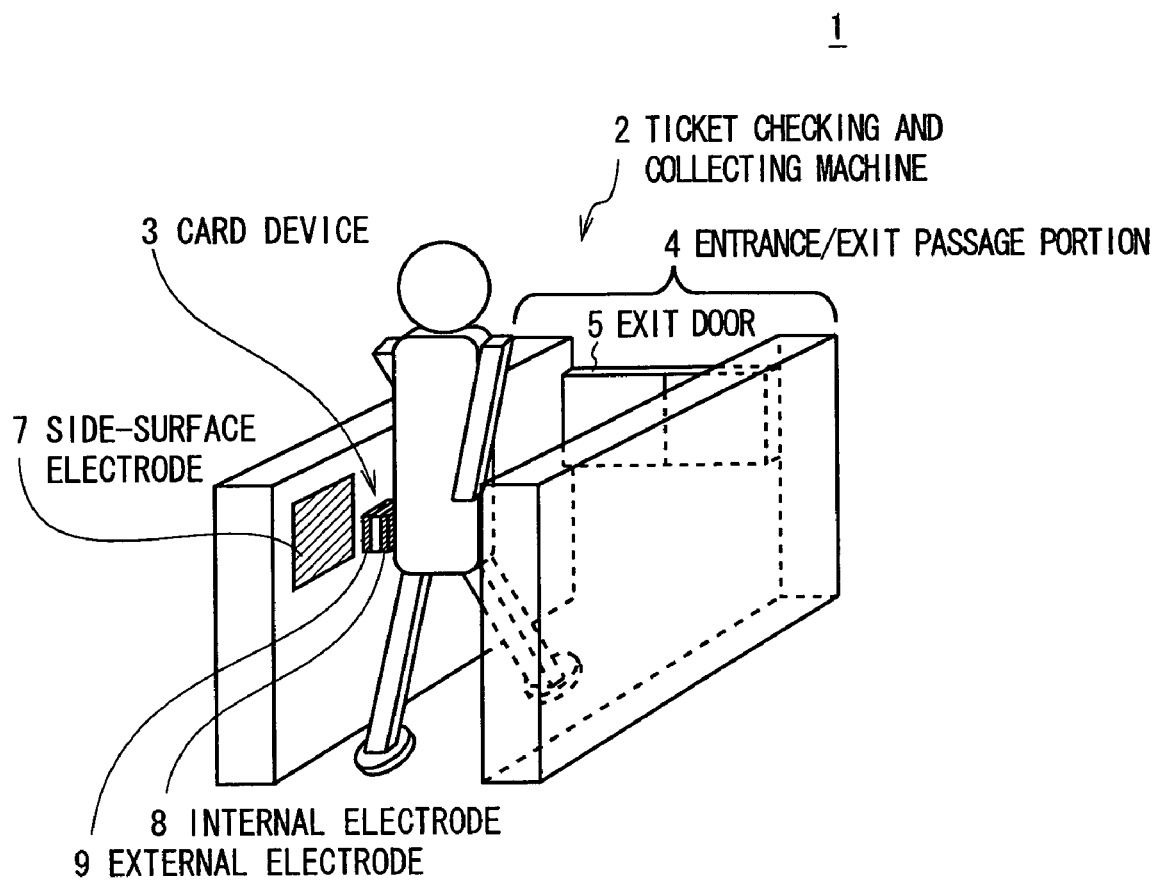
FIG. 5 is a schematic diagram showing the entire configuration of a communication system according to a first embodiment.

(2) First Embodiment (2-1) Entire Configuration of a Communication System According to a First Embodiment In FIG. 5, reference numeral 1 generally denotes the entire configuration of the communication system according to the first embodiment. The communication system comprises a ticket checking and collecting machine 2 provided at a particular station, and a mobile device of a card shape (hereinafter referred to as a card device) 3, which is inserted in a pocket of the clothes over a human body (hereinafter referred to as a user) who utilizes the ticket checking and collecting machine 2.

The ticket checking and collecting machine 2 is provided with an entrance/exit passage portion 4 installed at a predetermined place in the station as a passage for the user and an exit door 5 openably and closably provided at the exist side of the entrance/exit passage portion 4. There is provided an electrode (hereinafter referred to as a side-face electrode) 7 at the side face of the entrance side of the entrance/exit passage portion 4.

The card device 3 is provided with an electrode (hereinafter referred to as an internal electrode) 8 on one of the surfaces thereof and an electrode (hereinafter referred to as an external electrode) 9 on the other surface.

The communication system 1 is adapted to activate the card device 3 of the user who is passing through the entrance/exit passage portion 4, perform near field communication between the card device 3 and the ticket checking and collecting machine 2, and open the exit door 5 which is in a closed condition, if necessary.

(2-2) Near Field Communication

The near field communication performed in the communication system 1 is now described below in detail using a figures showing the internal configuration of the ticket checking and collecting machine 2 and the internal configuration of the card device 3.

(2-2-1) Activation of a Card Device

Figure 6:
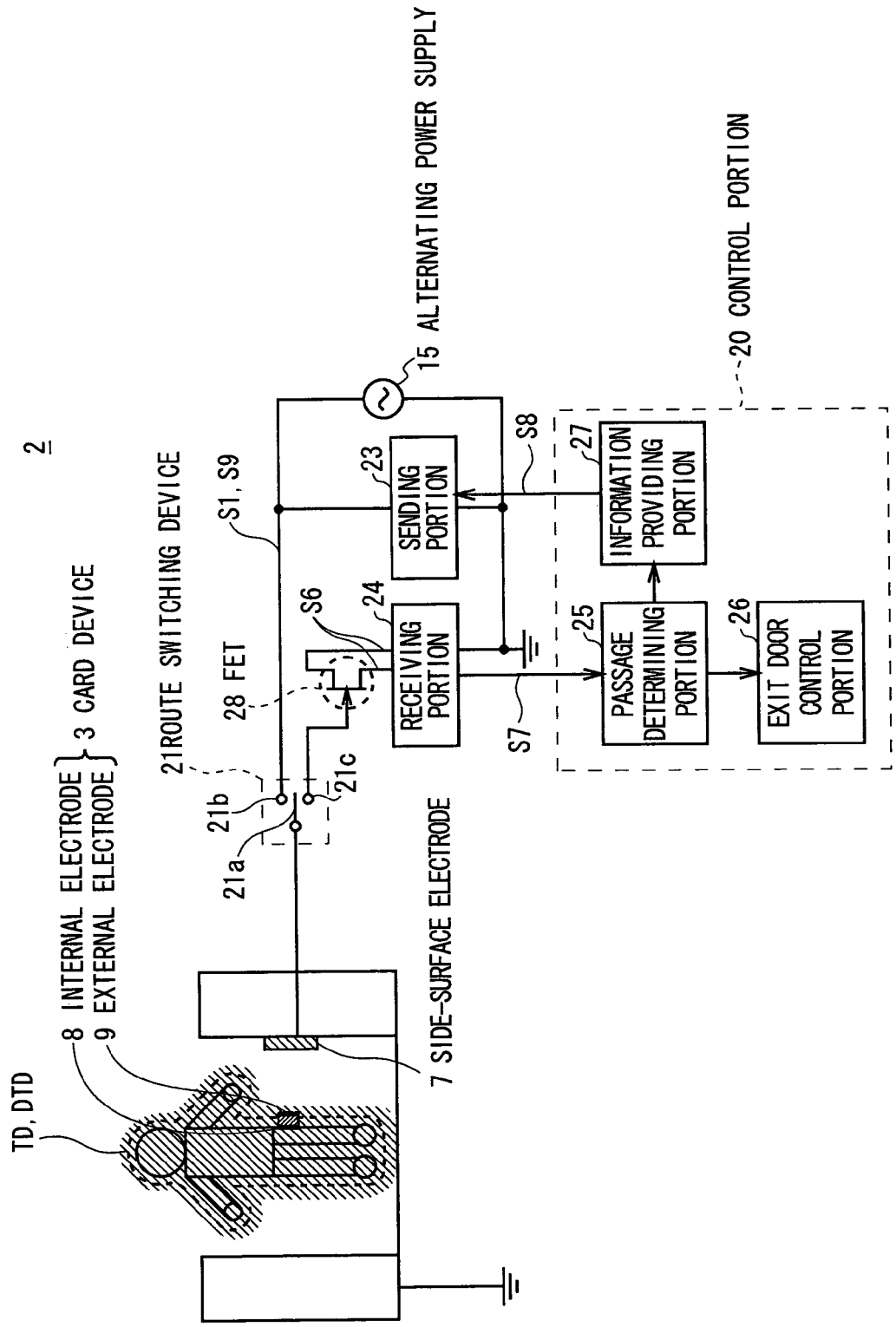
FIG. 6 is a schematic/block diagram showing the configuration of a ticket checking and collecting machine.

As shown in FIG. 6, a control portion 20 of the ticket checking and collecting machine 2 is adapted to perform overall control of the ticket checking and collecting machine 2 in accordance with a predetermined communication processing program and is adapted to switch a switching section 21a of a route switching device 21 to a sending connection edge 21b or a receiving connection edge 21c based on a predetermined communication clock prestored in an information storage memory.

A sending portion 23, at a sending timing based on the communication clock, supplies an alternating signal S1 with a predetermined frequency generated based on an alternating power supply 15, to the side-surface electrode 7 via the route switching device 21 to generate a quasi-electrostatic field, which oscillates according to the alternating signal S1 via the side-surface electrode 7.

Specifically, the sending portion 23 is adapted to generate a quasi-electrostatic field from the side-surface electrode 7 while preventing a radiation field and an induction field, as described above with reference to FIGS. 2 and 3, by generating the alternating signal S1 with a frequency f and supplying the signal S1 to the side-surface electrode 7, the frequency f satisfying the following formula which is obtained by substituting the above formula (10) into the above formula (12), with the relative permittivity of the air $\epsilon$ assumed to be 1, the wave length in the air denoted by $\lambda$, the maximum distance between the external electrode 9 and the side-face electrode 7 when the card device 3 and the ticket checking and collecting machine 2 communicate with each other: denoted by r, and the frequency of the alternating signal S1 denoted by f, and rearranging the formula (12) after the substitution:

$$f < \frac{c}{2\pi \cdot r} \tag{13}$$

In this situation, when the user enters the inside of the quasi-electrostatic field generated from the side-surface electrode 7 (that is, when the user attempts to pass through the entrance/exit passage portion 4), the user within the quasi-electrostatic field is electrified according to the displacement of the side-surface electrode 7 and thereby acts as an antenna while a quasi-electrostatic field according to the displacement (hereinafter referred to as an alternating quasi-electrostatic field) TD isotropically spreads around the surface of the user.

Figure 7:
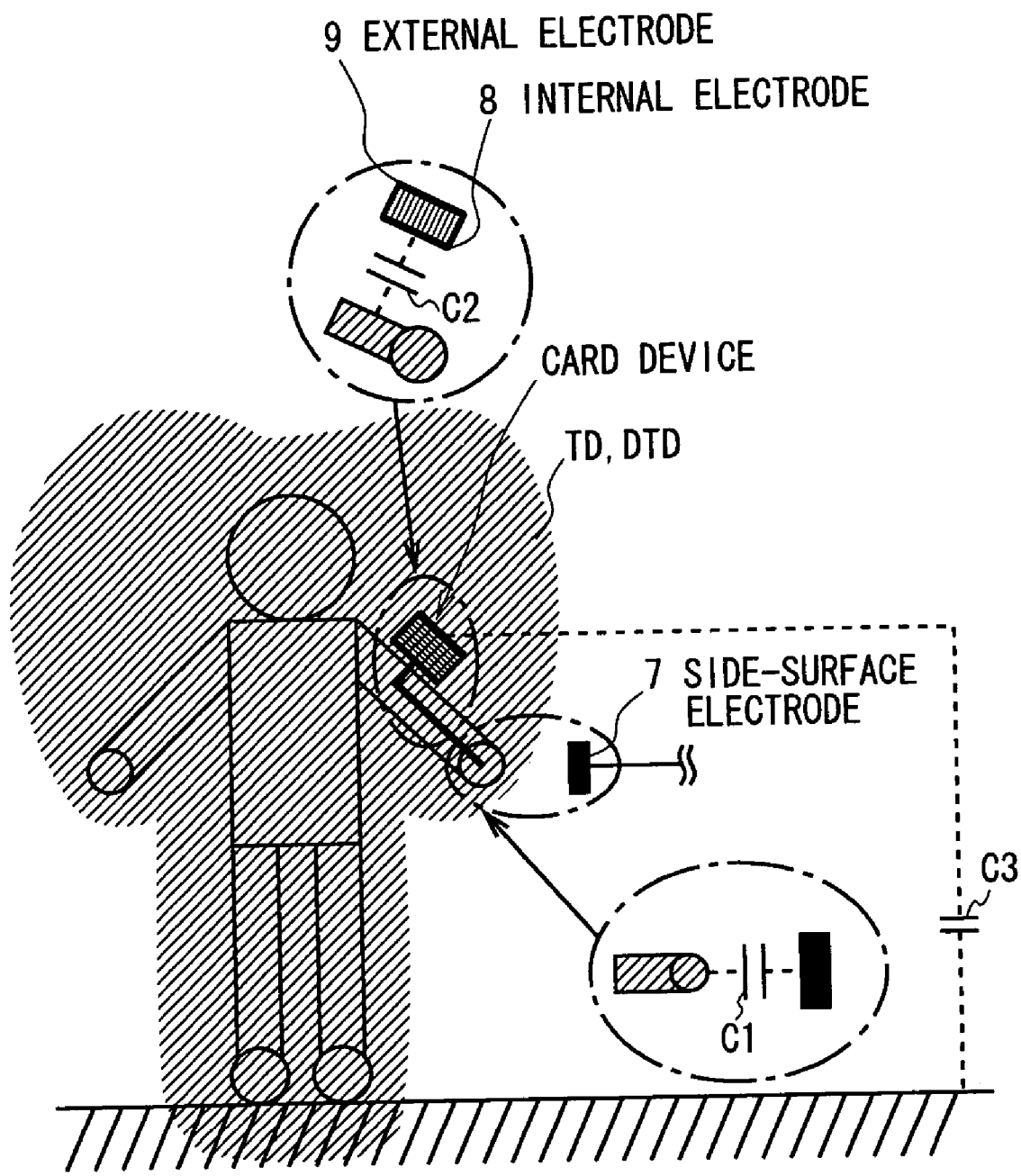
FIG. 7 is a schematic diagram provided to explain the action of a human body as an antenna.

In this case, as shown in FIG. 7, the internal electrode 8 of the card device 3 carried by the user is statically coupled with the user to form a capacitor C2, while the external electrode 9 is statically coupled with the ground to form a capacitor C3 and statically coupled with the side-surface electrode 7 (with a potential equivalent to that of the ground) via the user to form a capacitor C1.

Figure 8:
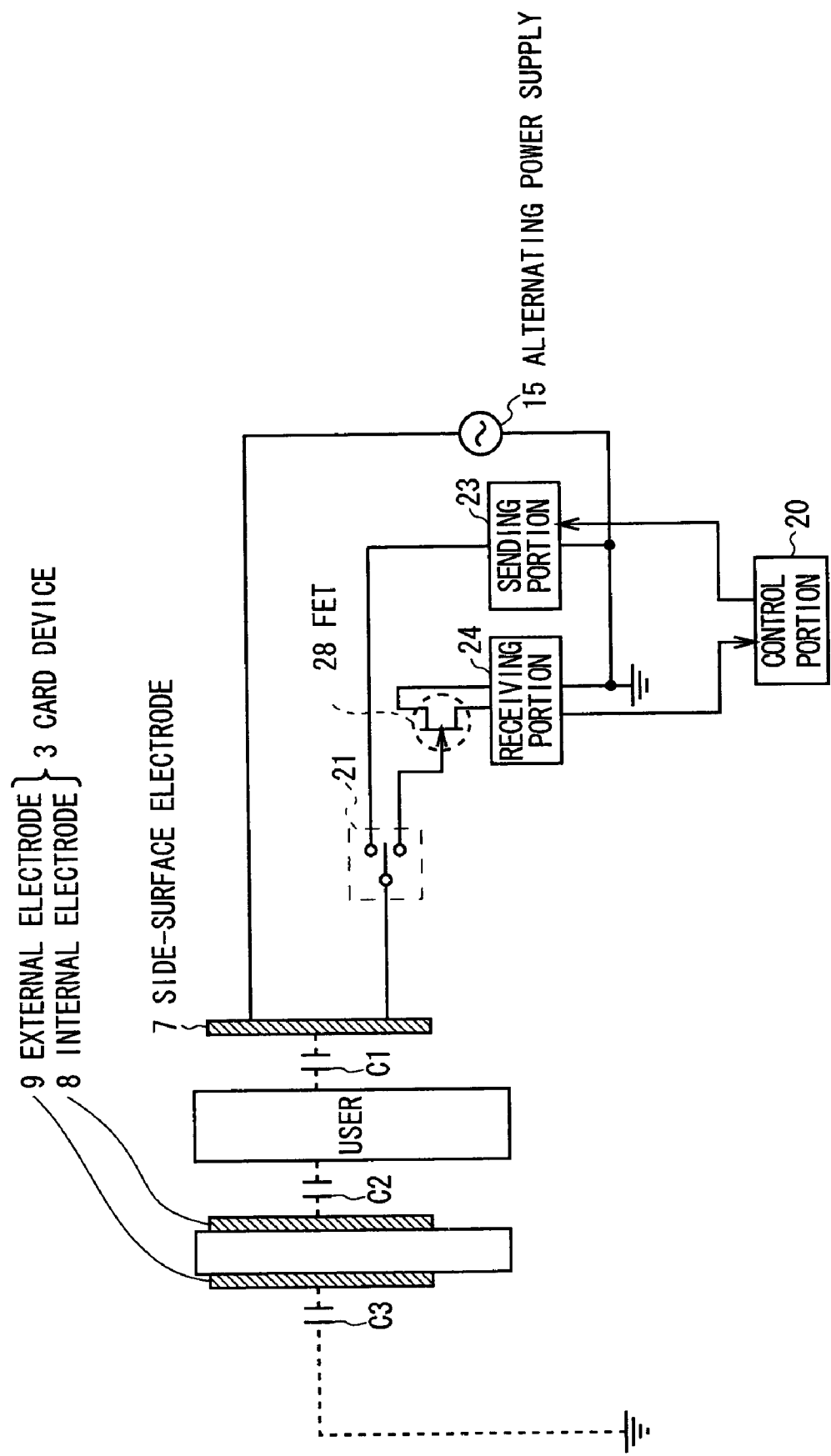
FIG. 8 is a schematic diagram showing electrical connection relations in the communication system.

As a result, as shown in FIG. 8, there is formed an electrical route sequentially via the side-surface electrode 7, the user, the internal electrode 8 and the external electrode 9, and the external electrode 9 provides a reference potential for the alternating power supply 15 in the card device 3 via the electrified user. Thereby, the voltage of the alternating power supply 15 on the ticket checking and collecting machine 2 side is applied between the internal-electrode 8 and the external electrode 9 in the card device 3 via the electrified user.

Figure 9:
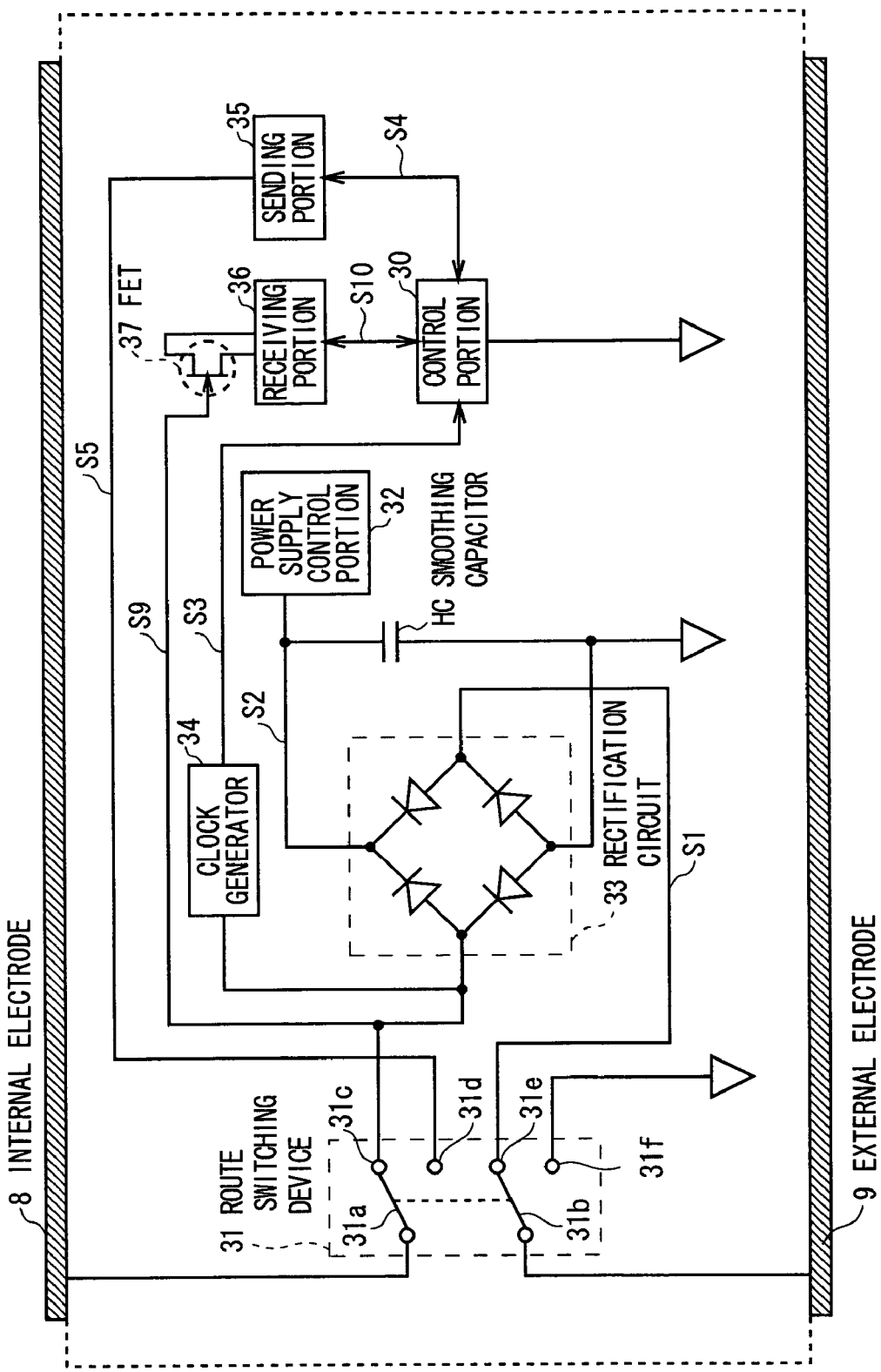
FIG. 9 is a circuit block diagram showing the configuration of a card device.

In this case, as shown in FIG. 9, the card device 3 connects a switching section 31a on the internal electrode 8 side with a receiving connection edge 31c, and a switching section 31b of the external electrode 9 with a receiving connection edge 31e; full-wave rectifies the alternating signal (current) S1 generated between the external electrode 9 and the internal electrode 8 by a rectification circuit 33; and a resultant direct current S2 is stored in a smoothing capacitor HC as power.

A power supply control portion 32 is adapted to activate the card device 3 when it detects that the power stored in the smoothing capacitor HC has reached a predetermined voltage level.

In this way, in the communication system 1, by electrifying a user to obtain power for the card device 3 from the user functioning as a huge antenna (electrode), supply of power from the ticket checking and collecting machine 2 can be assisted, and it is possible, on the card device 3 side, to obtain power without depending on the electrode area of the internal electrode 8 and the external electrode 9 and without providing a battery for the card device 3.

In achieving this, the communication system 1 is adapted to enhance efficiency of power supply from the ticket checking and collecting machine 2 to the card device 3 and enable miniaturization of the entire system and the card device 3 itself.

The card device 3 generates a synchronized clock S 3 corresponding to the communication clock of the ticket checking and collecting machine 2 with a clock generator 34, based on the frequency f of the alternating signal S1 supplied by the ticket checking and collecting machine 2, and supplies the synchronized clock S3 to a control portion 30.

The control portion 30 is adapted to perform overall control of the card device 3 in accordance with a predetermined communication processing program, and switches the switching sections 31a and 31b of the receiving-connection edge 31 based on the synchronized clock S3 supplied by the clock generator 34.

The control portion 30 is adapted to connect the switching section 31a with the receiving connection edge 31d and the switching section 31b with a ground connection edge 31f in the case of a sending timing based on the synchronized clock S3, while it connects the switching section 31a with the receiving connection edge 31c and the switching section 31b with the receiving connection edge 31e in the case of a receiving timing.

(2-2-2) Near Field Communication from a Card Device to a Ticket Checking and Collecting Machine At a sending timing based on the synchronized clock S3, the control portion 30 reads, from an internal information storage memory (not shown), identification information S4 identifying whether or not to permit a user to enter or exit from a station, for example, such as a station name or train fare, and supplies the information to a sending portion 35.

The sending portion 35 generates an alternating signal with the same frequency as that of the ticket checking and collecting machine 2 based on the power stored in the smoothing capacitor HC; performs modulation processing on the alternating signal in accordance with a predetermined modulation method to superimpose the identification information S4 thereon; and supplies a resultant identification signal S5 between the internal electrode 8 and the external electrode 9 via the receiving connection edge 31.

In this case, the internal electrode 8 oscillates:according to the frequency of the identification signal S5 and generates a quasi-electrostatic field (identification signal S5) according to the oscillation. As a result, the user is electrified in response to the oscillation of the internal electrode 8, and there is formed a quasi-electrostatic field (hereinafter referred to as an information-transmission quasi-electrostatic field) DTD which the identification signal S5 has, isotropically around the user according to the oscillation.

In this case, the user and the side-surface electrode 7 are coupled with each other by the same action as in the case described with reference to FIGS. 7 and 8, and the information-transmission quasi-electrostatic field DTD is detected by the side-surface electrode 7.

In this way, in the sending portion 35, by changing the electrification condition of the user according to the quasi-electrostatic field (identification signal S5) generated from the internal electrode 8, in the space where the radiation field and the induction field are prevented, as described above in relation to the formula (12), it is possible to cause the user to act as an antenna and form an information-transmission quasi-electrostatic field DTD.

In this case, the receiving timing based on the communication clock is set for the ticket checking and collecting machine 2 (FIG. 6), and a field effect transistor (hereinafter referred to as a FET) 28 detects the strength displacement of the information-transmission quasi-electrostatic field DTD detected by the side-surface electrode 7 as change in potential via the gate of the FET 28, and supplies it to a receiving portion 24 as an identification signal S6 via an amplifier (not shown).

The receiving portion 24 performs demodulation processing on the identification signal S6 in accordance with a predetermined demodulation method to abstract identification information S7 and supplies it to a passage determining portion 25 of the control portion 20.

Receiving the identification information S7 from the receiving portion 24, the passage determining portion 25 performs a predetermined determination process based on the identification information S7 and determination information prestored in the information storage memory and determines whether or not to allow the user, who is attempting to pass through the entrance/exit passage portion 4 (FIG. 5), to pass it.

When obtaining a positive result that the user should be allowed to pass, the passage determining portion 25 gives a passage permission instruction to an exit door control portion 26 and an information providing portion 27. On the contrary, when obtaining a negative result that the user should not be allowed to pass, the passage determining portion 25 gives a passage refusal instruction to the exit door control portion 26 and the information providing portion 27.

When receiving a passage permission instruction from the passage determining portion 25, the exit door control portion 26 opens the exit door 5 of the entrance/exit passage portion 4 (FIG. 5) to allow the user to pass. On the contrary, when receiving a passage refusal instruction from the passage determining portion 25, the exit door control portion 26 keeps the exit door 5 of the entrance/exit passage portion 4 closed to prevent the user from passing.

(2-2-3) Nearfield Communication from a Ticket Checking and Collecting Machine to a Card Device Receiving a passage permission instruction or a passage refusal instruction from the passage determining portion 25, the information providing portion 27 generates notification information S8 to be notified to the user, such as permission or passage refusal and other information, and then supplies the notification information to the sending portion 23 at a sending timing based on the communication clock.

The sending portion 23 performs modulation processing on the alternating signal S1 in accordance with a predetermined modulation method to superimpose the notification information S8 thereon, and supplies a resultant notification signal S9 to the side-surface electrode 7 via the route switching device 21 to generate a quasi-electrostatic field, which oscillates according to the notification signal S9, from the side-surface electrode 7.

Consequently, the sending portion 23 can change the electrification condition of the user according to the quasi-electrostatic field (the notification signal S9 ) to cause the user to act as an antenna, and form the information-transmission quasi-electrostatic field DTD in the neighborhood of the user, in the space where the radiation field and the induction field are prevented due to induction of the quasi-electrostatic field as described above with reference to FIGS. 7 and 8, In this case, in the card device 3 (FIG. 9), the receiving timing is based on the synchronized clock S3 is set, and the internal electrode 8 detects the information-transmission quasi-electrostatic field DTD formed in the neighborhood of the user. A FET 37 detects displacement of the strength of the information-transmission quasi-electrostatic field DTD detected by the internal electrode 8 as change in potential via the gate of the FET 37, and supplies it to the receiving portion 24 as the notification signal S9 via an amplifier (not shown).

The receiving portion 24 performs demodulation processing on the notification signal S9 in accordance with a predetermined demodulation method to abstract notification information S 10 and supplies it to the control portion 30.

In this case, the control portion 30 notifies the user of the contents of the notification information S10, for example, by displaying the contents via a display portion (not shown) based on the notification information S10.

In this way, the ticket checking and collecting machine 2 (the card device 3) can avoid receiving the notification signal S9 (the identification signal S5) that it has sent via the side-surface electrode 7 (the internal electrode 8) (so-called signal sneaking) by performing a half-duplex method in which a sending route and a receiving route are alternately switched based on the communication clock (the synchronized clock S3) to send and receive information.

In this case, the ticket checking and collecting machine 2 (the card device 3) can use both of the function of a electrification-inducing electrode for electrifying a user and the function of a detection electrode for detecting change in the electrification condition of the user caused by the card device 3 (the ticket checking and collecting machine 2) with only one side-surface electrode 7 (internal electrode 8), and thereby the ticket checking and collecting machine 2 can be miniaturized.

Furthermore, the ticket checking and collecting machine 2 can use one alternating signal S1 both for power supply and for information communication such that one side-surface electrode 7 can be used both as a sending electrode for a signal for power supply and as a receiving electrode for a signal for information communication without providing such electrodes separately, and thereby the ticket checking and collecting machine 2 can be miniaturized.

(2-3) Auxiliary Means in Near Field Communication

Figure 10:
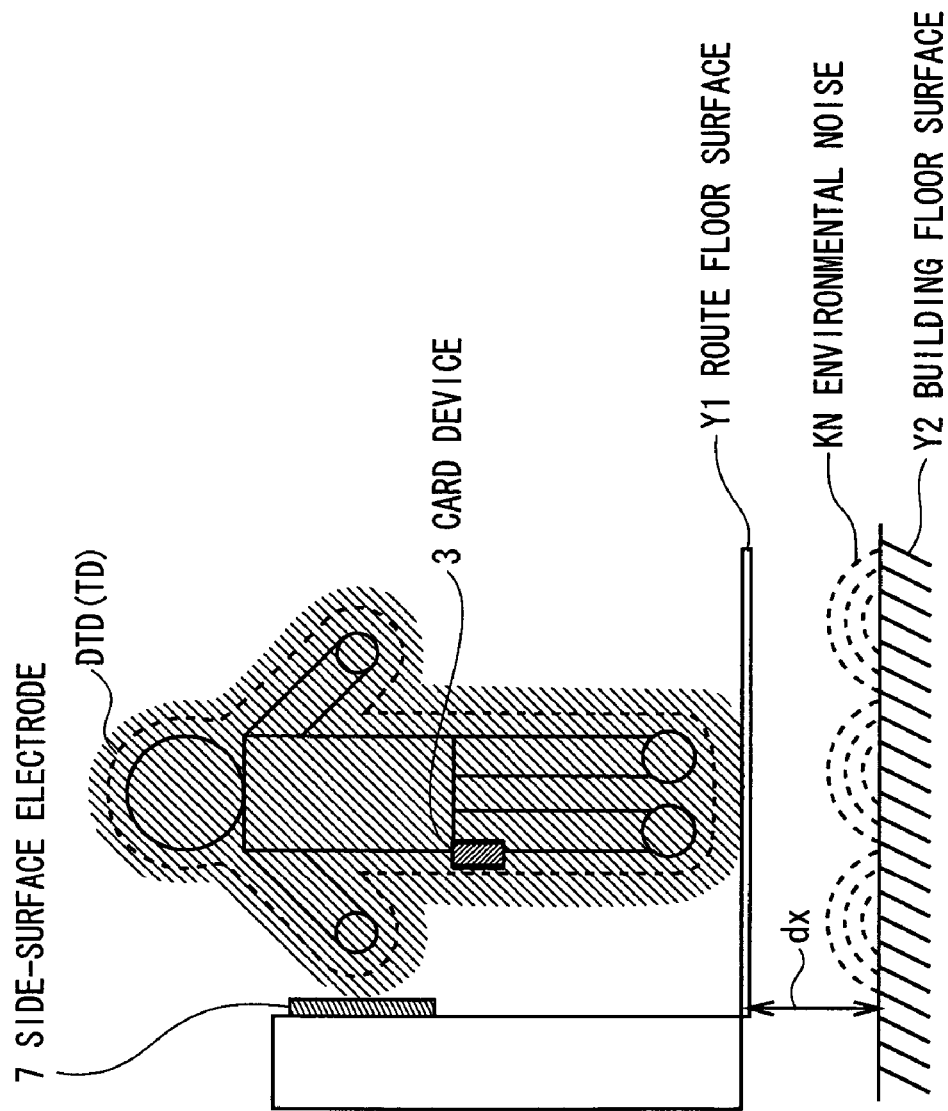
FIG. 10 is a schematic diagram provided to explain the floor surface of the ticket checking and collecting machine.

In addition to the above configuration, as shown in FIG. 10, in the communication system 1, a floor surface (hereinafter referred to as a route floor surface) Y1 of the entrance/exit passage portion 4 is provided in such a condition that it is not grounded to the ground (hereinafter referred to as a building floor surface) Y2 but is separated from the building floor surface Y2 by predetermined space dx (a gap).

In this case, the electrostatic capacity between the feet of the user and the building floor surface Y2 can be reduced to be less than the electrostatic capacity between the user and the side-surface electrode 7 by the amount corresponding to the space dx between the route floor surface Y1 and the building floor surface Y2, and thereby leakage of the information-transmission quasi-electrostatic field DTD (alternating quasi-electrostatic field TD) from the feet to the building floor surface Y2 can be prevented.

In addition to this, it is also possible to prevent noises (hereinafter referred to as environmental noises) KN caused by inconsistency of the building floor surface Y2, such as electrical discharge noises caused by electrically unstable condition due to a gap between joint surfaces of steel material in the building floor surface Y2 or rust of the steel material, from being induced from the route floor surface Y1 to the user.

Thus, in the communication system, it is possible to form, in a more stable condition, the equipotential surface of an information-transmission quasi-electrostatic field DTD (an alternating quasi-electrostatic field TD) which is formed substantially isotropically from around the surface of the user when the user is electrified and the electrification change momentarily conducts over the periphery of the surface of the user, and therefore it is possible to stable near field communication.

Figure 11:
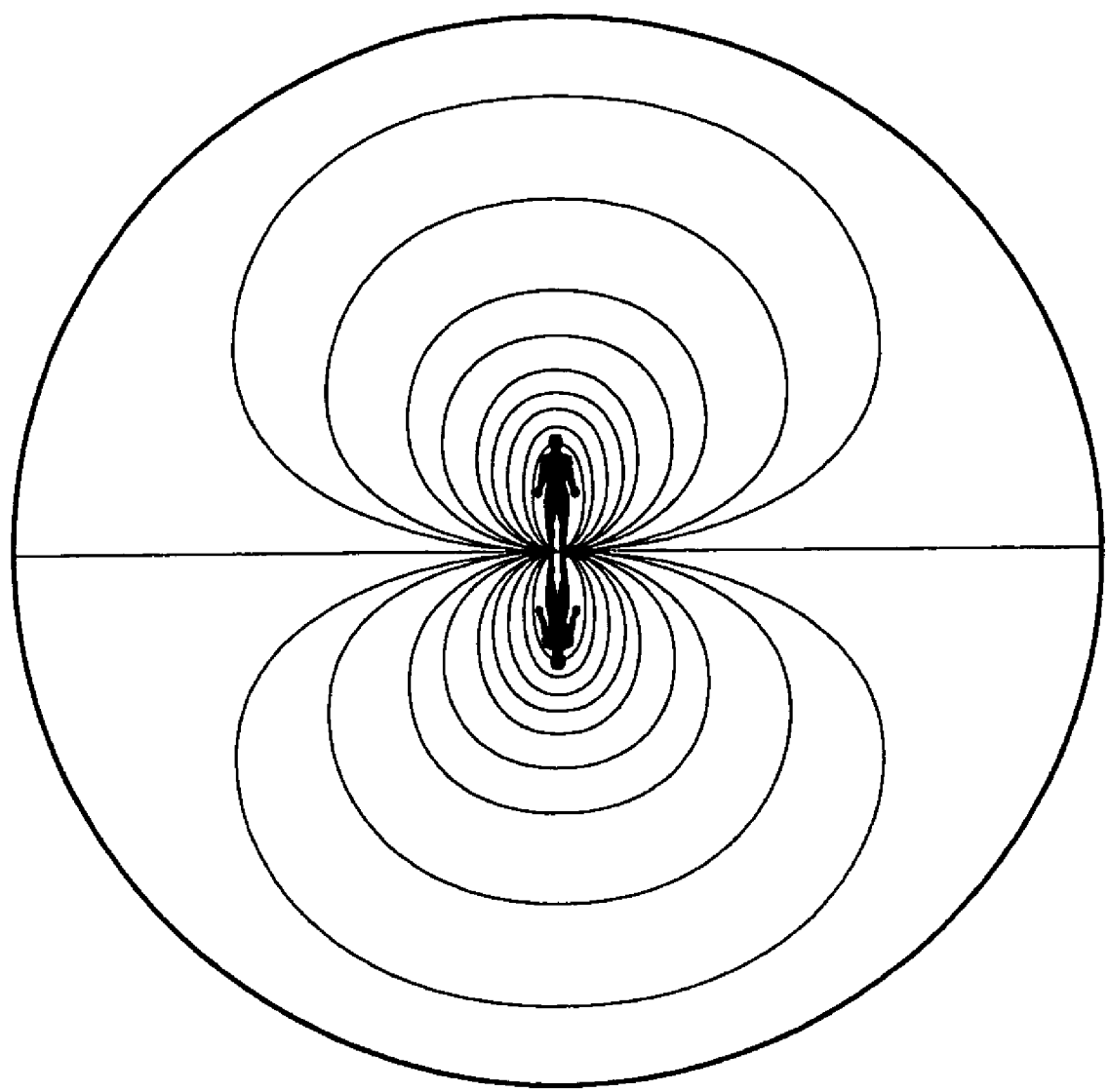
FIG. 11 is a schematic diagram showing the equipotential surface of a quasi-electrostatic field formed when a human body is caused to act as an ideal dipole-antenna.
Figure 12:
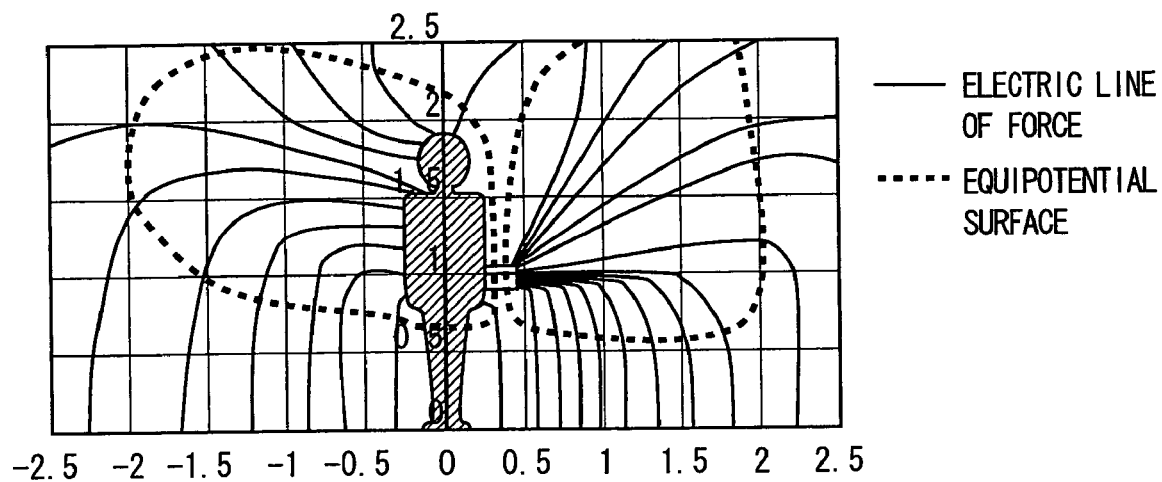
FIG. 12 is a schematic-diagram showing the equipotential surface of a quasi-electrostatic field formed according to this embodiment.
Figure 12:
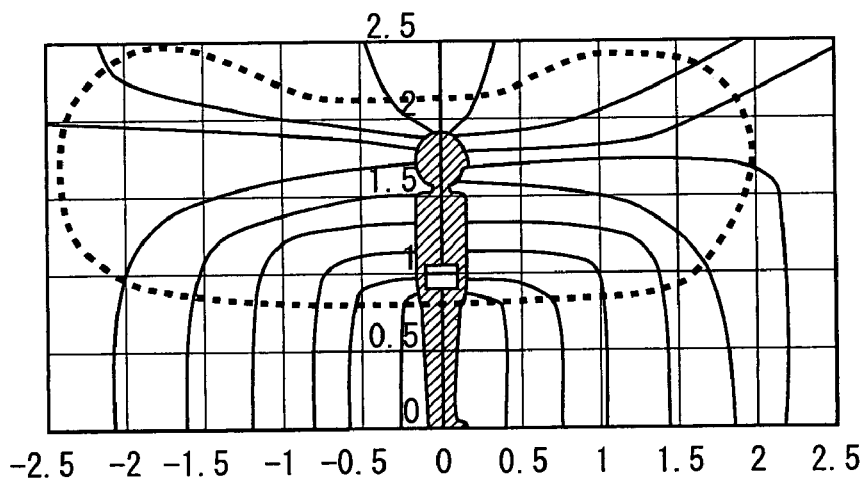

This will be visually apparent from comparison of FIG. 11 showing the equipotential surface of a quasi-electrostatic field when a human body functions as an ideal dipole antenna and FIG. 12 showing the results of experiments according to the present embodiment.

Figure 13:
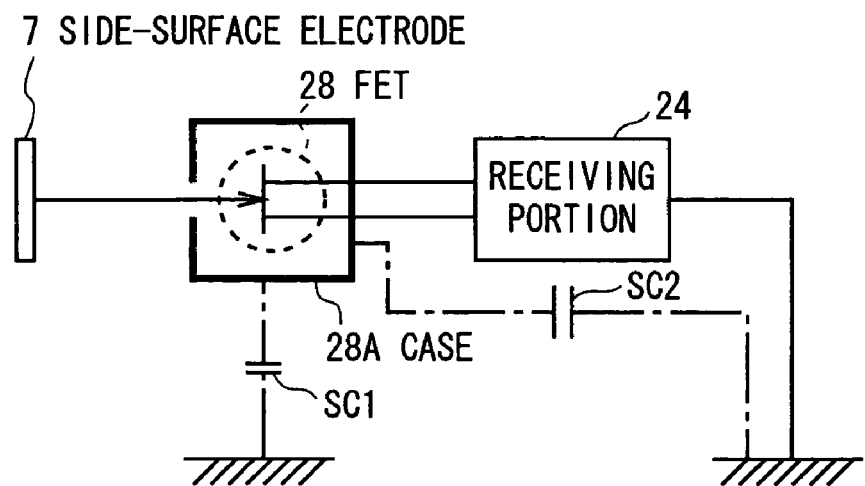
FIG. 13 is a schematic diagram provided to explain prevention of electrical leakage.

Furthermore, as shown in FIG. 13, the ticket checking and collecting machine 2 of the communication system 1 is adapted to prevent leakage of a signal on the route from the side-surface electrode 7 to the receiving portion 24 via the FET 28. Specifically, first, a case 28A, a conductor covering the periphery of the FET 28 is provided in a condition that it is electrically separated from the FET 28; and second, only the receiving portion 24 is grounded on the receiving route.

Third, as means for preventing such leakage, the ticket checking and collecting machine 2 is adapted to reduce the electrostatic capacity SC1 between the FET 28 and the ground in comparison with the electrostatic capacity SC2 on the route from the FET 28 to the receiving portion 24 via the receiving portion 24, for example, by increasing the interval (height) between the FET 28 and the ground.

Thus, the ticket checking and collecting machine 2 can efficiently induce the information-transmission quasi-electrostatic field DTD (alternating quasi-electrostatic field TD) detected by the side-surface electrode 7 to the receiving portion 24 via the FET 28, and thereby receive the information-transmission quasi-electrostatic field DTD (FIG. 5) formed by the user with high sensitivity.

(2-4) Operation and Effect

In the communication system 1 with the above configuration, utilizing the nature of a quasi-electrostatic field and the nature of a user (human body), the user is electrified to act as an antenna, and a quasi-electrostatic field which is consequently formed in the neighborhood of the user is used as an information transmission medium.

Specifically, on the card device 3 (the ticket checking and collecting machine 2) side in the communication system 1, a quasi-electrostatic field according to the identification signal S5 (the notification signal S9) modulated according to the identification information S4 (the notification information S8) is generated from the internal electrode 8, (the side-surface electrode 7) to electrify the user, as described above with reference to FIGS. 6 and 9. In the ticket checking and collecting machine 2 (the card device 3), change in the strength of an information-transmission quasi-electrostatic field DTD (FIG. 5) isotropically formed in the neighborhood of the user is detected via the side-surface electrode 7 (the internal electrode 8) and the FET 28 (the FET 37) sequentially, and the identification information S4 (the notification information S8) is demodulated based on the detection result.

Accordingly, in the communication system 1, it is possible to form an information-transmission quasi-electrostatic field DTD that spreads substantially isotropically from the surface of the user according to the identification signal S5 (the notification signal S9), with the user who is electrified very desirably. Furthermore, sending and receiving is possible without depending on the way of holding or mounting the card device 3 and without depending on whether or not the internal electrode 8 of the card device 3 is in contact with the user.

Furthermore, in the communication system 1, since the electrified user is caused to act as an antenna, it is possible to form an information-transmission quasi-electrostatic field DTD that spreads isotropically from the surface of the user, irrespective of the movement of the user, and therefore, it is possible to send and receive information without forcing the user to perform a predetermined movement in communication.

Furthermore, in the communication system 1, since the electrified user is caused to act as an antenna and, via a non-propagating information-transmission quasi-electrostatic field DTD consequently formed in the neighborhood of the user, information is sent and received, it is possible to avoid interference with other radio waves (an induction field or a radiation field) and avoid interception from outside the communication space to secure confidentiality of the communication contents.

In this way, in the communication system 1, by causing the user intervening between sending and receiving electrodes to act as an antenna rather than treating the user as a medium as has been done conventionally, it is possible to realize sending and receiving of information without directional restrictions in the neighborhood of the user, with confidentiality secured and without forcing the user to perform a predetermined movement.

In addition to the above configuration, in the communication-system 1, the relation between the maximum distance r and the frequency f of the signal to be supplied to the side-surface electrode 7 is selected to satisfy the above formula (13), as described above with reference to the formula (12).

Accordingly, in the communication system 1, when causing a user who is going to pass through the entrance/exit passage portion 4 to act as an antenna to perform near field communication, the communication space can be formed as space (substantially closed space) where the non-propagating quasi-electrostatic field E3θ is always dominant. As a result, the communication output can be weakened to the degree that the communication contents are not propagated outside the communication space, and thereby confidentiality of the communication contents are secured more sufficiently.

According to the above configuration, in the communication system 1, utilizing the nature of a quasi-electrostatic field and the nature of a human body, the user is electrified to act as an antenna, and an information-transmission quasi-electrostatic field DTD which is consequently formed in the neighborhood of the user is used as an information transmission medium. Thus, it is possible to realize sending and receiving of information without directional restrictions in the neighborhood of the user, with confidentiality secured and without forcing the user to perform a predetermined movement, and thereby the degree of freedom in communication using a quasi-electrostatic field can be enhanced.

(2-5) Other Embodiments

Figure 14:
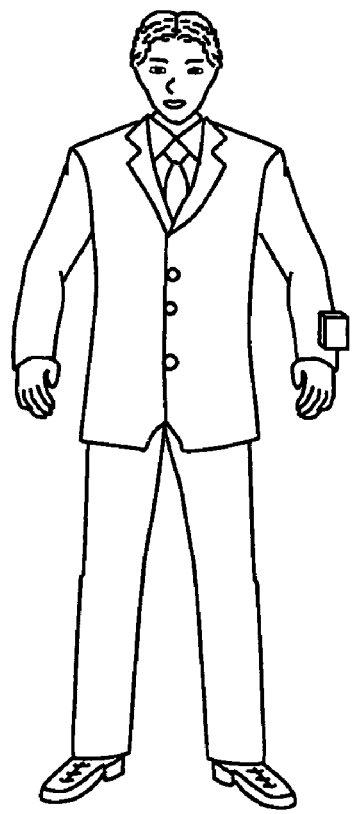
FIG. 14 is a schematic diagram showing an example of mounting the card device in another embodiment.
Figure 15:
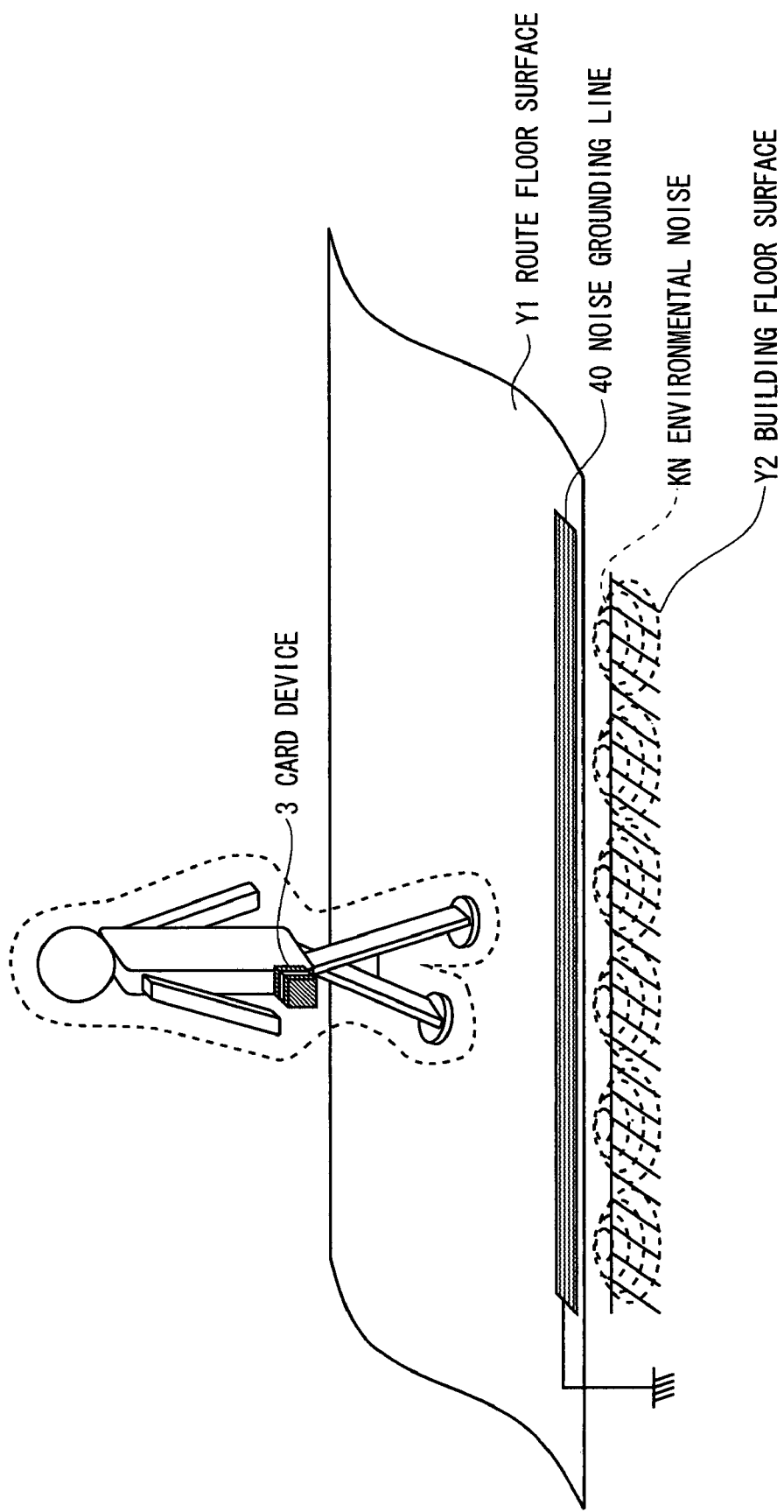
FIG. 15 is a schematic diagram showing the configuration of a noise absorption/grounding line.

In the first embodiment described above, description has been made on the case where the card device 3 as a first communication device is inserted in a pocket of the clothes of a user. The present invention, however, is not limited thereto, and the card device 3 may be fitted around the arm as shown in FIG. 14. Alternatively, it may be incorporated in a mobile telephone or a pedometer, or may be put in a bag. That is, the card device 3 can be provided in the neighborhood of the sending or receiving human body without depending on the way of holding or mounting it and without depending whether or not the internal electrode 8 of the card device 3 is in contact with the user, as described above. After all, the only requirement is that the card device 3 should be in the neighborhood of the user.

Description has been made on the case where the card device 3 is of a card shape in the first embodiment described above. However, the present invention is not limited thereto, and the card device 3 may be of other various shapes.

Furthermore, in the first embodiment described above, description has been made on the case where the route floor surface Y1 is provided for the entrance/exit passage portion 4 in a condition that it is separated from the building floor surface Y2 (FIG. 10) by predetermined spaced x. The present invention, however, is not limited thereto, and a member with a low relative permittivity may be filled between the route floor surface Y1 and the building floor surface Y2.

In this case, if the relative permittivity of the member filled between the route floor surface Y1 and the building floor surface Y2 is assumed to be ε, the gap between the route floor surface Y1 and the building floor surface the building floor surface Y2 is assumed to be dx, the permittivity of vacuum electric constant is assumed to be ε0, and the area of the user's soles is assumed to be S, then the electrostatic capacity CY2 between the user's feet and the building floor surface Y2 approximates the value obtained from the relation represented by the following formula:

$$CY2 = \varepsilon_0 \cdot \varepsilon \frac{S}{dx} \quad (14)$$

Therefore, if the distance dx between the route floor surface Y1 and the building floor surface Y2 and the relative permittivity ε of the member filled between the route floor surface Y1 and the building floor surface Y2 are selected in consideration of the above relation, the electrostatic capacity CY2 between the user's feet and the building floor surface Y2 can be certainly less than the electrostatic capacity between the user and the side-surface electrode 7. Thereby, leakage of the information-transmission quasi-electrostatic field DTD (alternating quasi-electrostatic field TD) from the user's fee to the building floor surface Y2 can be prevented more securely, and near field communication can be stabilized more securely.

In the first embodiment described above, description has been made on the case where the route floor surface Y1 is provided for the entrance/exit passage portion 4 in a condition that it is separated from the building floor surface Y2 (FIG. 10) by predetermined space dx, as coupling preventing means for preventing the identification target and the building floor from being electrically coupled with each other. The present invention, however, is not limited thereto, and there may be provided a noise absorption grounding line 40 laid on the route floor surface Y1 and grounded to the building floor surface Y2, as shown in FIG. 16.

In this case, it is possible to prevent such noises (hereinafter referred to as environmental noises) KN as are caused by inconsistency of the building floor surface Y2 from being induced from the route floor surface Y1 to the user and thereby stabilize the near field communication, similarly to the first embodiment described above. Furthermore, if not only the space dx but also the noise absorption grounding line 40 is provided between the route floor surface Y1 (FIG. 10) and the building floor surface Y2, stabilization of the near field communication can be enhanced more.

Furthermore, in the first embodiment described above, description has been made on the case where the side-surface electrode 7 as a detection electrode and a power supply electrode uses one alternating signal S1 both as a power supply signal and as a carrier signal. The present invention, however, is not limited thereto, and an electrode for power supply and an electrode for information communication may be separately provided.

Figure 16:
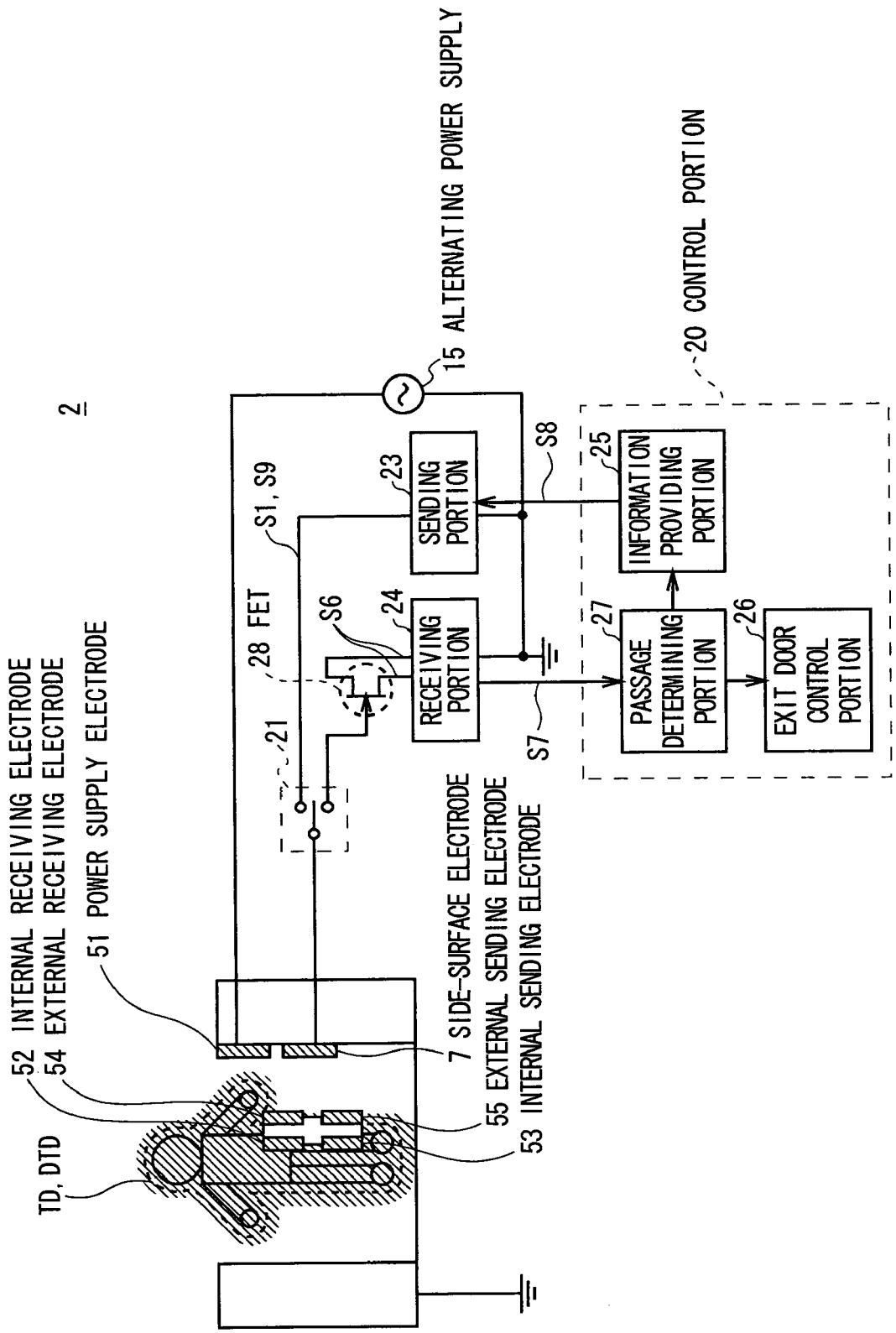
FIG. 16 is a schematic/block diagram showing the configuration (1) of a ticket checking and collecting machine in another embodiment.
Figure 17:
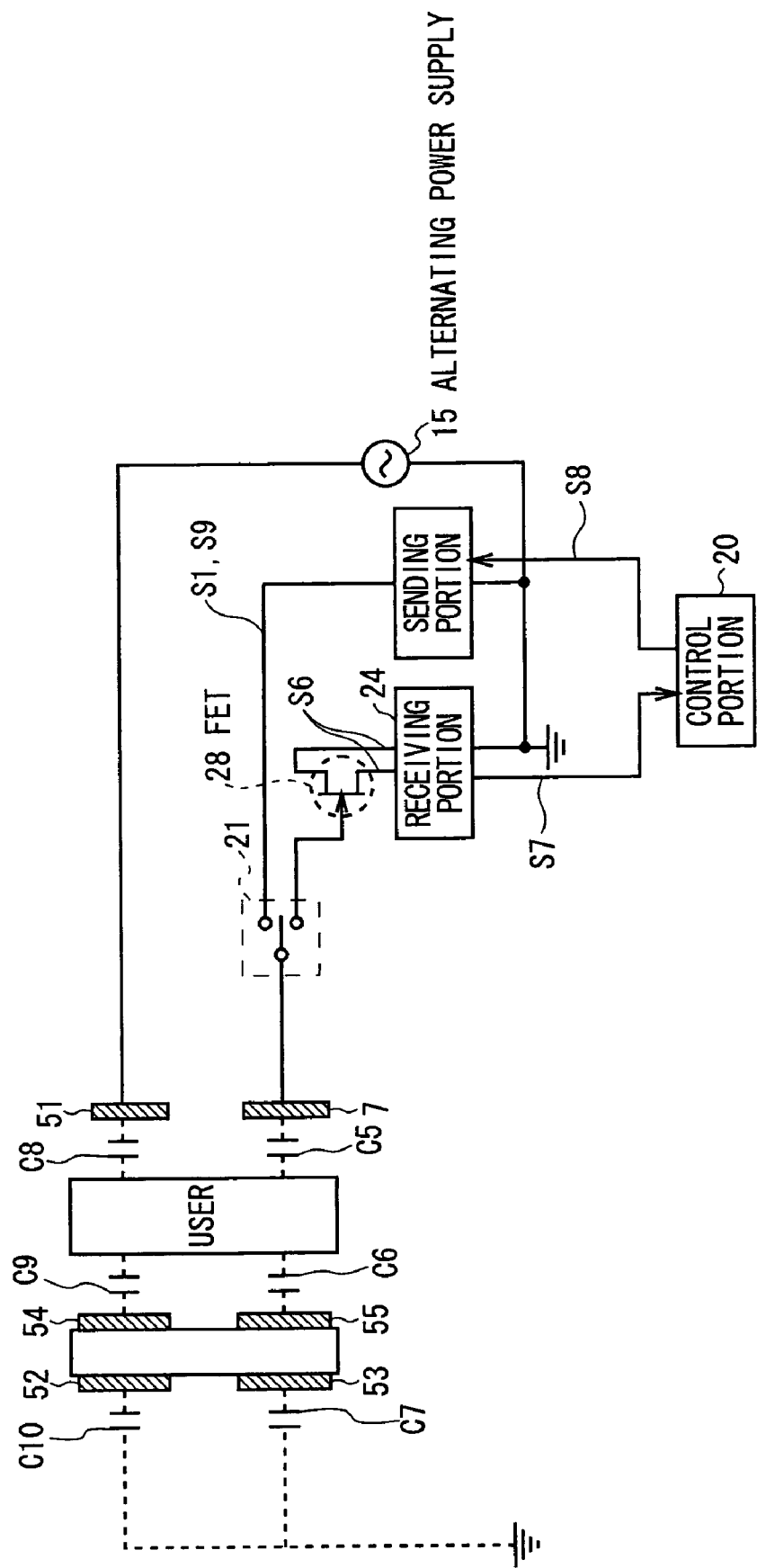
FIG. 17 is a schematic diagram showing electrical connection relations (1) in a communication system in another embodiment.
Figure 18:
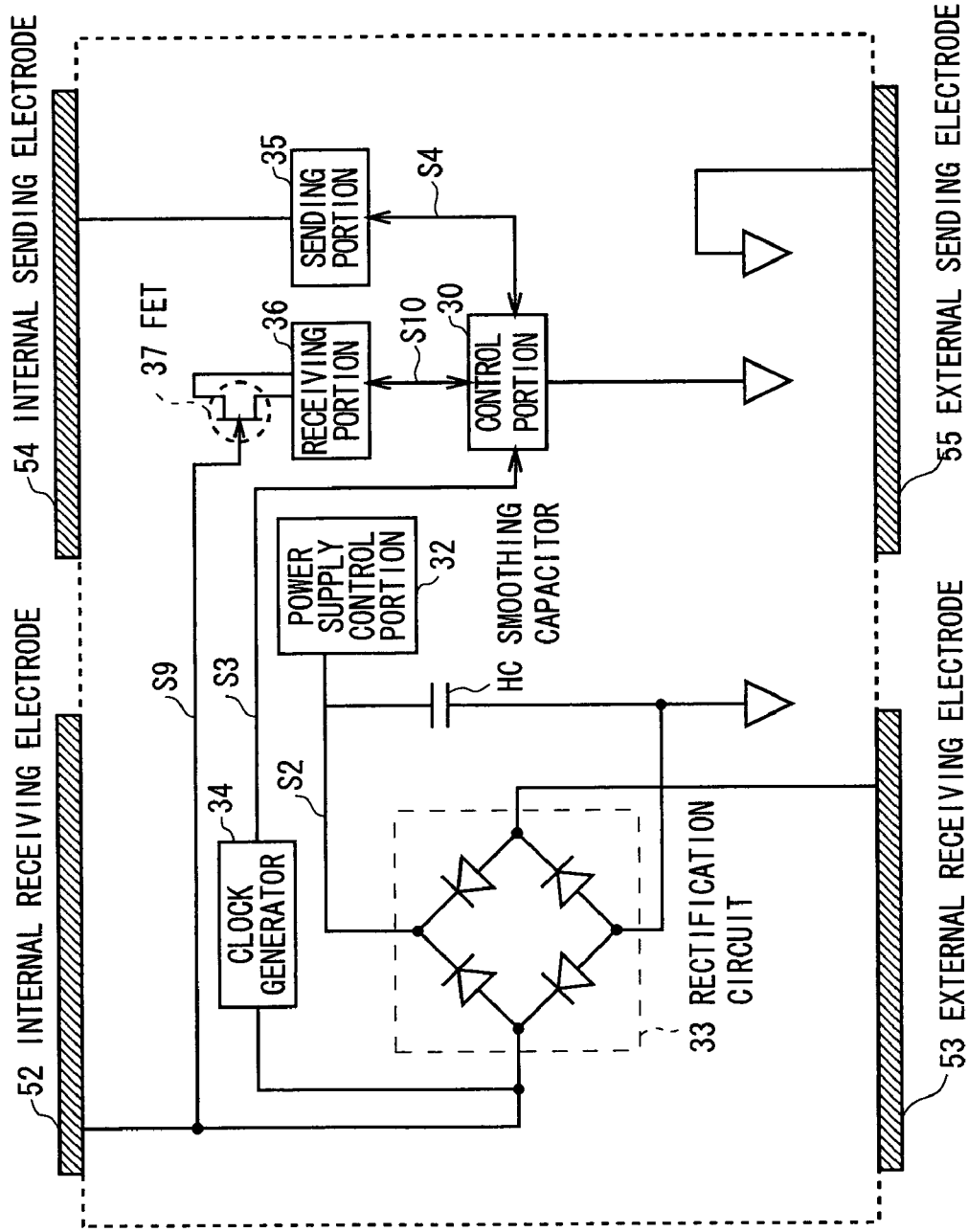
FIG. 18 is a circuitry block diagram showing the configuration of a card device in another embodiment.

Specifically, as shown in FIGS. 16, 17 and 18 in which the portions corresponding to the portions in FIGS. 6, 8 and 9 are denoted by the same reference numerals and characters, in the ticket checking and collecting machine 2, there is newly provided a power supply electrode 51 on the internal surface of the entrance/exit passage portion 4 at the entrance side, separately from the side-surface electrode 7, and the alternating power supply 15 is provided between the power supply electrode 51 and the ground. The side-surface electrode 7 is used only for near field communication. In the card device 3, there is provided an internal receiving electrode 52 and an internal sending electrode 53 on one surface and an external receiving electrode 54 and an external sending electrode 55 on the other surface, instead of the route switching device 31. If sending and receiving on the power supply route and sending and receiving on the information communication route are separately performed between the ticket checking and collecting machine 2 and the card device 3 as described above, the same effect as that of the above-mentioned embodiment can be obtained.

Furthermore, in the first embodiment described above, description has been made on the case where change in the electrification condition (an information-transmission quasi-electrostatic field DTD) of a user that the side-surface electrode 7 as a detection electrode has detected, is detected as identification information S7 by the FET 28 as detection means, and the identification information S7 is demodulated by the receiving portion 24 as modulation means. The present invention, however, is not limited thereto, and the identification information S7 may be demodulated by measuring change in the impedance of the information-transmission quasi-electrostatic field DTD.

Figure 19:
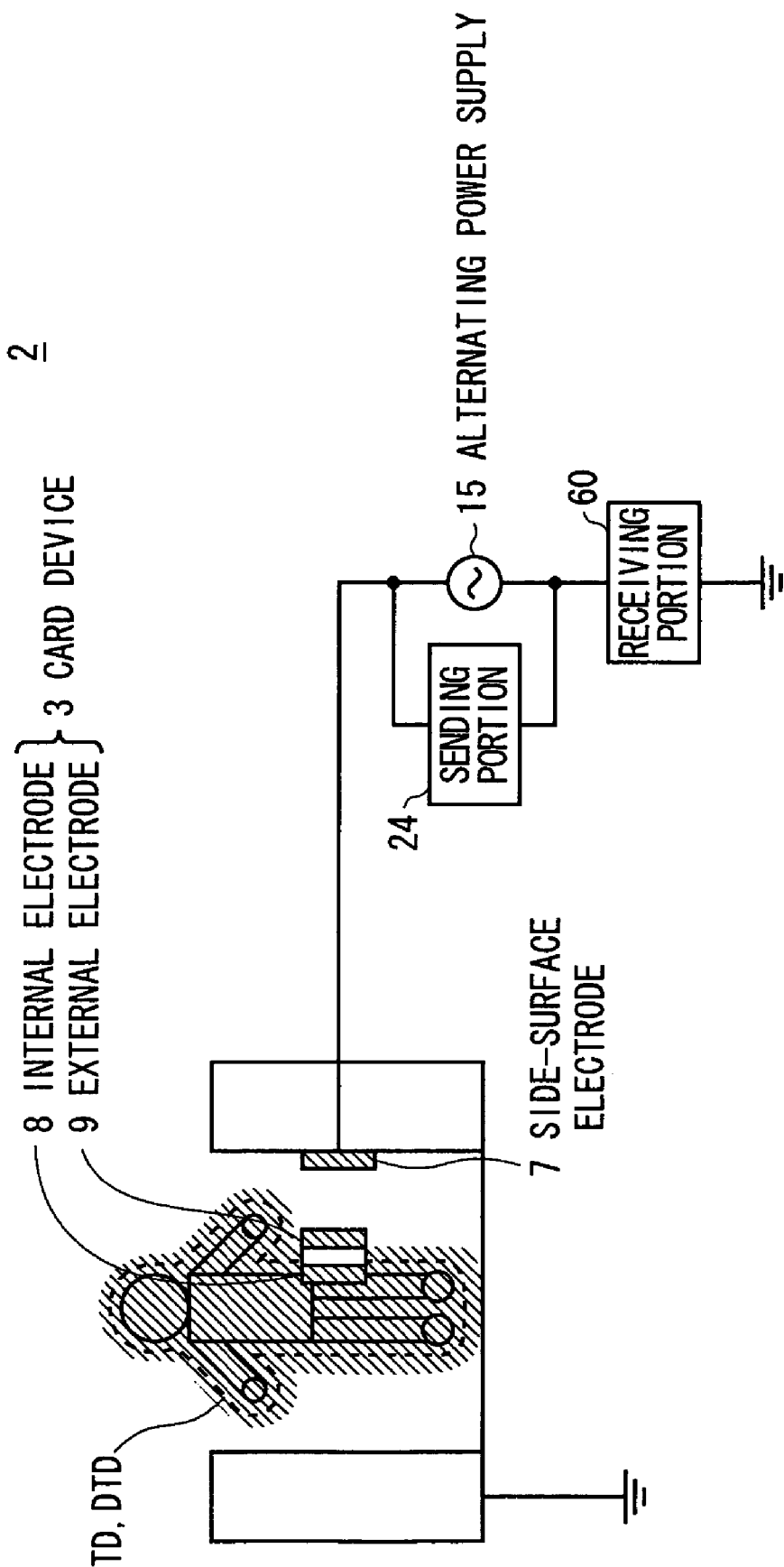
FIG. 19 is a schematic/block diagram showing the configuration (2) of a ticket checking and collecting machine in another embodiment.

Specifically, as shown in FIG. 19 in which the portions corresponding to those in FIG. 6 are denoted by the same reference numerals, the ticket checking and collecting machine 2 supplies the alternating signal S1 with a predetermined frequency generated based on the alternating power supply 15, to the side-surface electrode 7 via the route switching device 21, using the sending portion 23 to generate a quasi-electrostatic field. Consequently, a receiving portion 60 as demodulation and impedance measuring means can obtain the same effect as that of the embodiment described above.

Furthermore, in the first embodiment described above, description has been made on the case where change in the electrification condition of a user is detected by the FET 28 or 37 as an identification signal S6 (notification signal S9). The present invention, however, is not limited thereto, and the change in the electrification condition of the user may be detected by various other detection means such as an induction-electrode-type field strength meter for measuring the voltage induced by induction voltage by means of configuration with a transistor or a FET, an induction-electrode-type modulation-amplification-system field strength meter for AC converting a direct signal obtained by an induction electrode using a chopper circuit, oscillation capacity and the like, an electro-optic-effect-type field strength meter for applying en electric field to material having an electro-optic effect to measure change in the light propagation characteristics caused in the material, and, only for the card device 3, an electrometer, a shunt-resistor-type field strength meter, a current-collection-type field strength meter and the like.

Furthermore, in the first embodiment described above, description has been made on the case where the alternating signal S1 is continuously supplied by the sending portion 23 as modulation and power supply means to the side-surface electrode 7. The present invention, however, is not limited thereto, and the alternating signal S1 may be supplied to the side-surface electrode 7 only while the side-surface electrode 7 as a detection electrode detects field displacement caused by the user according to the user's walking motion when the user is coming near to the entrance/exit passage portion 4.

Specifically, the ticket checking and collecting machine 2, under the control of the control portion 20, connects the switching section 21a of the route switching device 21 with the receiving connection edge 21c until it detects a user who is going to pass through the entrance/exit passage portion 4 (FIG. 5), detects displacement of the walking quasi-electrostatic field caused by the user coming near to the entrance/exit passage portion 4, via the side-surface electrode 7 and the FET 28 sequentially, and, when sending the detection result to the sending portion 23, connects the switching section 21a with the sending connection edge by the control portion 20 to give the alternating signal S1 to the side-surface electrode 7. On the other hand, when the ticket checking and collecting machine 2 cannot detect the displacement of the walking quasi-electrostatic field caused by the user going away from the entrance/exit passage portion 4, via the side-surface electrode 7 and the FET 28 sequentially, and therefore does not send the detection result to the sending portion 23 any more, it connects the switching section 21a with the receiving connection edge 21c again by the control portion 20 and stops supply of the alternating signal S1 to the side-surface electrode 7. Thus, the ticket checking and collecting machine 2 does not supply the alternating signal S1 to the side-surface electrode 7 except while it detects the displacement of the walking quasi-electrostatic field (electrification) caused by the user's walking motion, and thereby energy saving can be more enhanced in comparison to the embodiment described above.

Furthermore, in the first embodiment described above, description has been made on the case where near field communication is performed between the card device 3 as a first communication device of a mobile type provided in the neighborhood of a user, and the ticket checking and collecting machine 2 as a second communication device provided at a predetermined control target. The present invention, however, is not limited thereto, and near field communication may be performed between a card device 3 provided on one user and a card device 3 provided on the other card device 3 via the one or the other user. In this case, the number of users (human bodies) via which the near field communication is performed from the card device 3 provided on the one user to the card device 3 provided on the other user may be any number. In this case, the same effect as that of the embodiment described above can be obtained.

Furthermore, in the first embodiment described above, description has been made on the case where the ticket checking and collecting machine 2 is applied to the present invention as a second communication device provided at a predetermined control target. The present invention, however, is not limited thereto, and a second communication device provided on or near a video tape recorder, a television set, electronics such as a mobile telephone or a personal computer, medical equipment, an automobile, a desk, and other control targets to be controlled, for example. In this case the same effect as that of the embodiment described above can be obtained.

Furthermore, in the first embodiment described above, description has been made on the case where a human body is applied to the present invention as an identification target. The present invention, however, is not limited thereto, and organisms such as mammals, reptiles, plants, even predetermined conductive material, and any other object with an electrification properties to be identified may be broadly applied to the present invention as an identification target.

Furthermore, in the first embodiment described above, description has been made on the case where the present invention is applied to the communication system 1 which opens the exit door 5 as necessary for allowing entrance into or exit from the entrance/exit passage portion 4 as a communication route. The present invention, however, is not limited thereto and can be broadly applied to communication systems for various other purposes, such as a communication system for opening a door as necessary for allowing entrance into or exit from the entrance/exit passage of a company, a communication system with a communication route in the neighborhood of the desk, for opening the door of a desk as necessary when a user comes near to the desk, a communication system with a communication route in the neighborhood of a personal computer, for powering on the personal computer when a user comes near to the personal computer, and a communication system using the conveyance passage for conveying a predetermined identification target as a communication route, for switching the conveyance passage-as necessary when the identification target is conveyed to a predetermined position, that is, any communication system that electrifies a human body to cause the human body to act as an antenna and performs sending and receiving of information using a quasi-electrostatic field formed in the neighborhood of the human body as an information transmission medium.

Figure 20:
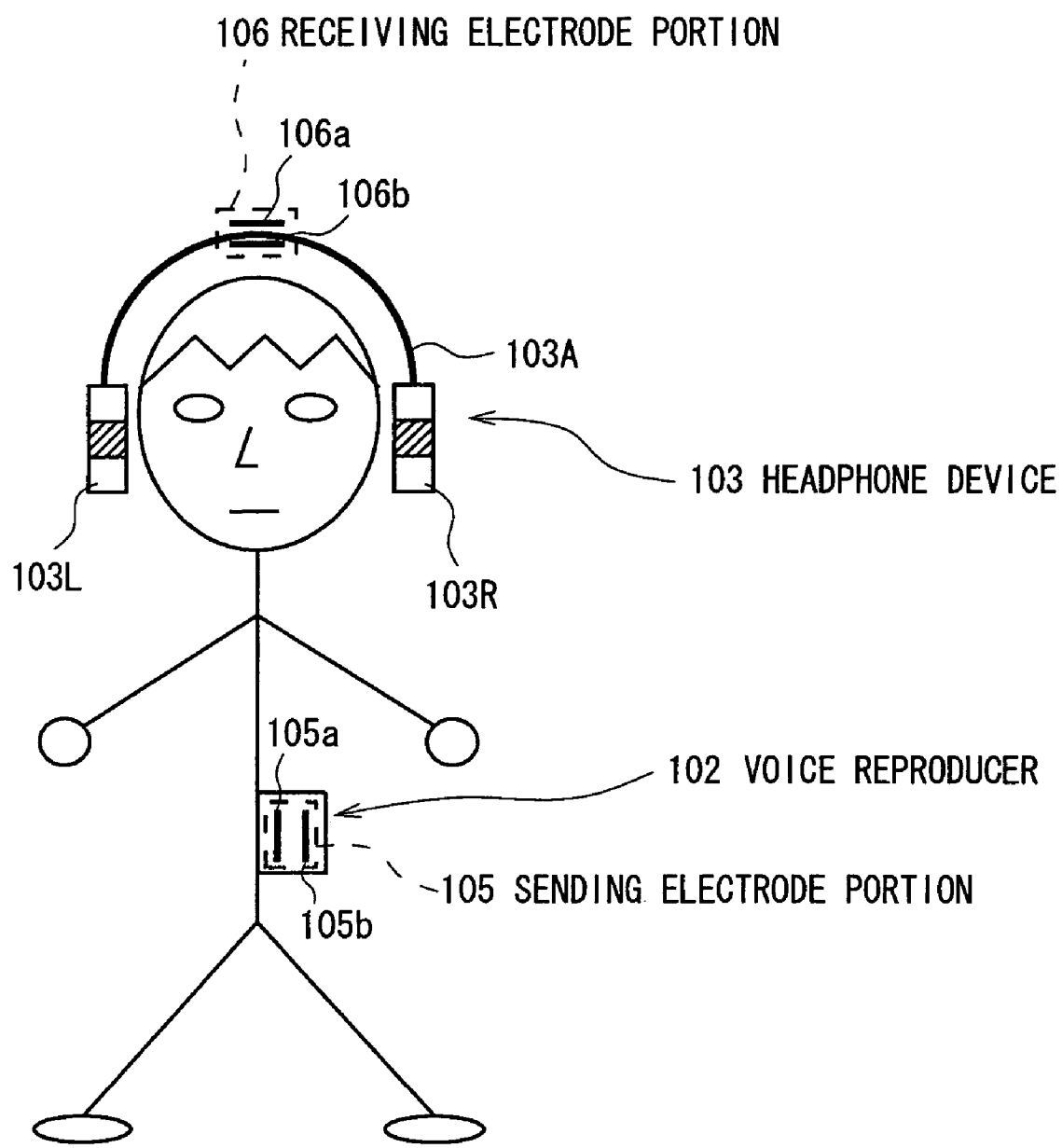
FIG. 20 is a schematic diagram showing the entire configuration of a communication system according to a second embodiment.

(3) Second Embodiment (3-1) Entire Configuration of a Communication System According to a Second Embodiment In FIG. 20, reference numeral 100 denotes the entire communication system according to a second embodiment, which comprises a voice reproducer 102 inserted in a hip pocket of clothes over a human body and a headphone device 103 fitted on the head of the human body.

The voice reproducer 102 is of a card shape, and there is provided a parallel plate electrode portion (hereinafter referred to as a sending electrode portion) 105 comprising a sending electrode 105a and a reference electrode 105b paired with the sending electrode 105a within the voice reproducer 102.

In this case, the voice reproducer 102 reproduces a voice signal from a voice storage medium and generates a quasi-electrostatic field modulated according to the reproduced voice signal from the sending electrode portion 105 and thereby electrifies the human body.

The headphone device 103 comprises a hair band portion 103A and a pair of ear pad portions 103L and 103R provided at the ends of the hair band portion 103A. The hair band portion 103A is provided with a parallel plate electrode portion (hereinafter referred to as a receiving electrode portion) 106 comprising a receiving electrode 106a located generally at the center thereof and a reference electrode 106b paired with the receiving electrode 106a.

In this case, the headphone device 103 detects change in the electrification condition of the human body electrified by the voice reproducer 102 as change in the electric field near the receiving electrode portion 106, specifically the potential difference between the electrodes 106a and 106b of the receiving electrode portion 106, demodulates a voice signal obtained as the result, and then outputs voice based on the voice signal from speakers (not shown) included in the ear pad portions 102L and 102R.

As described above, the communication system 100 is adapted to detect a quasi-electrostatic field generated from the sending electrode portion 105 of the voice reproducer 102 as the potential difference between the electrodes 106a and 106b of the receiving electrode portion 106 of the headphone device 103 to enable near field communication of a voice signal to be performed via a human body.

In the first embodiment described above, near field communication is performed by utilizing the potential difference between the electrode provided on the human body (the internal electrode 8) and the electrode (the side-surface electrode 7) provided at a predetermined place (on the entrance/exit passage portion 4). However, since the phases of the signal which reaches the device on the receiving side via the human body and the signal received from the electrode of the device on the receiving side via the electric field formed in the air are physically opposite, the signals counteract with each other, and therefore sometimes they cannot be received.

Especially on the sending side, an induction field and a radiation field, which are not easily attenuate relative to the distance in comparison with a quasi-electrostatic field, cause waste of sending power, and the merit of being "difficult to propagate far", a characteristic of near field communication, cannot be obtained due to these fields.

Therefore, in this embodiment, in the communication 100, the voice reproducer 102 as a transmitter and the headphone device 103 as a receiver are designed such that the radiation field and the induction field are to be below the noise floor level and the potential difference between the electrodes 106a and 106b of the receiving electrode portion 106, at a position where use of the receiving electrode portion 106 is assumed, exceeds a level detectable by a preamplifier 121.

Consequently, the communication system 100 can optimize energy required for near field communication to be performed by the transmitter and the receiver (the voice reproducer 102 and the headphone device 103), and can prevent unnecessary propagation and improve spatial resolution to enforce stabilization of communication.

(3-2) Configuration of a Voice Reproducer

Figure 21:
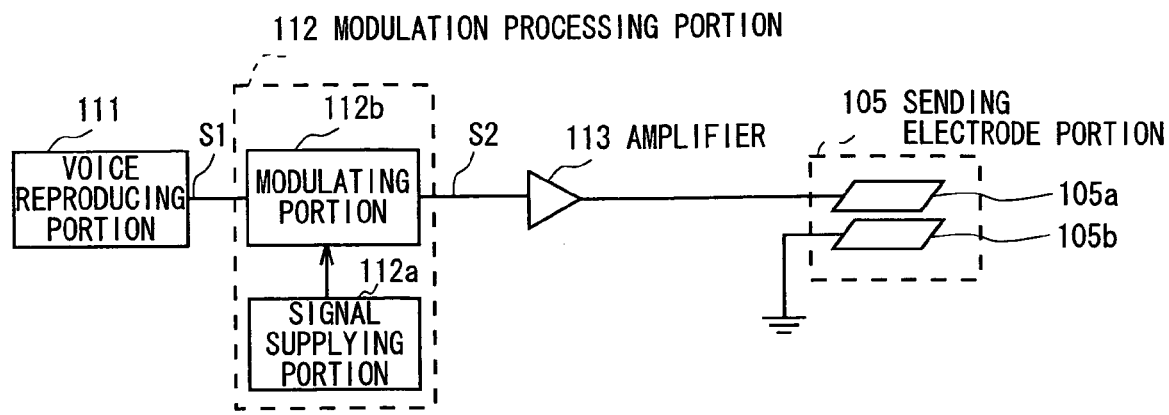
FIG. 21 is a block diagram showing the configuration of a voice reproducer.

The voice reproducer 102 comprises a voice reproducing portion 111, a modulation processing portion 112, an amplifier 113 and a sending electrode portion 105, as shown in FIG. 21.

The sending electrode portion 105 is of an electrode structure (electrode shape, electrode area and distance between electrodes) selected in accordance with a designing approach for a transmitter and a receiver and a transmitter to be described later. Specifically, it is formed in an electrode structure according to the reference frequency such that the strength of the induction field component of a generated electric field is below the noise floor specified according to the communication band.

The voice reproducing portion 111 reproduces a voice signal S1 from a voice storage medium mounted on a mounting portion not shown, and sends the reproduced voice signal S1 to the modulation processing portion 112.

The modulation processing portion 112 comprises a signal supplying portion 112a and a modulating portion 112b. For the signal supplying portion 112a, a potential corresponding to a prespecified originating frequency (working frequency) is set as the potential of a voltage signal to be applied to the sending electrode portion 105.

The signal supplying portion 112a is adapted to supply a voltage signal with the specified originating frequency and potential to the modulating portion 112b at a predetermined timing. The modulating portion 112b is adapted to perform modulation processing on the voltage signal in accordance with a predetermined modulation method to superimpose the voice signal S1 thereon and apply the resultant modulated signal to the sending electrode 105a of the sending electrode portion 105 via the amplifier 113.

In this case, the sending electrode 105a oscillates according to the originating frequency of the modulated signal S2; the human body is electrified by a quasi-electrostatic field which has been generated in response to the oscillation; and as a result, there is formed a quasi-electrostatic field according to the oscillation, almost isotropically around the human body.

In this way, the voice reproducer 102 is adapted to send information (a voice signal) via a human body.

(3-3) Configuration of a Headphone Device

Figure 22:
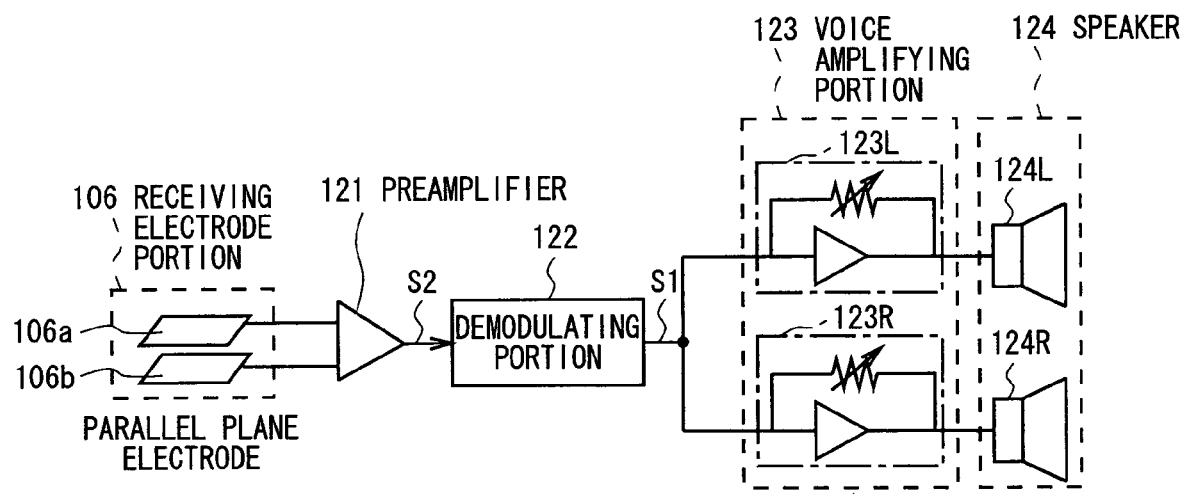
FIG. 22 is a block diagram showing the configuration of a head phone device.

The headphone device 103 comprises a receiving electrode portion 106, a preamplifier 121, a demodulating portion 122, a voice amplifying portion 123 (123L and 123R) and speaker 124 (124L and 124R), as shown FIG. 22.

The receiving electrode portion 106 is formed in an electrode structure selected in accordance with a designing approach for a transmitter and a receiver to be described later. Specifically, it is formed such that the strength of the induction field component of a generated electric field is below the noise floor specified according to the communication band, without depending on the electrode area, and with a distance between electrodes according to the reference frequency.

The preamplifier 121 detects the potential difference between the electrodes 106a and 106b of the receiving electrode portion 106 and sends it to the demodulating portion 122 as a modulated signal S2. It is desirable to use a preamplifier with a high input resistance as the preamplifier 121 since an input signal of a preamplifier is generally weak.

The demodulating portion 122 performs demodulation processing on the modulated signal S2 supplied by the demodulating portion 122 in accordance with a predetermined demodulation method and thereby generates a voice signal S1. It then sends the voice signal S1 to the speaker 124 (124L and 124R) via voice amplifying portion 123 (123L and 123R).

As a result, a voice based on the voice signal S1 is outputted from the speaker 124 (124L and 124R).

As described above, the headphone device 103 is adapted to release a voice based on the voice signal S1 sent from the voice reproducer 102.

(3-4) A Designing Method for a Transmitter and a Receiver

Description is now made on a designing method for the voice reproducer 102 as a transmitter and the headphone device 103 as a receiver.

(3-4-1) Designing Parameters

First, designing parameters in designing a transmitter and a receiver (the voice reproducer 102 and the headphone device 103) are now described below.

The transmitter and the receiver are designed with the following (A) and (B) as a guideline (hereinafter referred to as a designing guideline): (A) the induction field generated from the sending electrode portion 105 should be controlled to be below the noise floor; and (B) the potential obtained between the electrodes 106a and 106b of the receiving electrode portion 106 should be higher than the noise of the preamplifier 121 (FIG. 16) itself mounted on the receiver (the headphone device 103).

To design a transmitter and a receiver to satisfy the designing guideline, the following various designing parameters are selected in this descending order of importance as preprocessing for designing: (a) the originating frequency and the communication band, (b) the electrode area (including the electrode shape; hereinafter the same) and the distance between electrodes in the sending electrode portion 105, and the electrode area and the distance between electrodes in the receiving electrode portion 106, (c) the positions of the sending electrode portion 105 and the receiving electrode portion 106 on a human body, and (d) the preamplifier 121.

Actually, in selecting the various designing parameters (a) to (d), various conditions (hereinafter referred to designing conditions), such as the application of the communication system, the communication application used for communication, and even the space area enough for mounting the sending electrode portion 105 (the receiving electrode portion 106) onto the voice reproducer 102 (the headphone device 103), are taken into consideration.

(3-4-2) Potential Between Electrodes in a Receiving Electrode Portion

Description will be now made on the potential generated between the receiving electrode 106a and the reference electrode 106b of the receiving electrode portion 106 (hereinafter referred to as potential between electrodes).

The potential between electrodes of the receiving electrode portion 106 is an important element that means, so to speak, communication performance. The potential between electrodes was simulated with the FDTD method (Finite Difference Time Domain: a method for solving the Maxwell equation, which is a basic electromagnetic equation, with a finite difference and a time domain).

Figure 23:
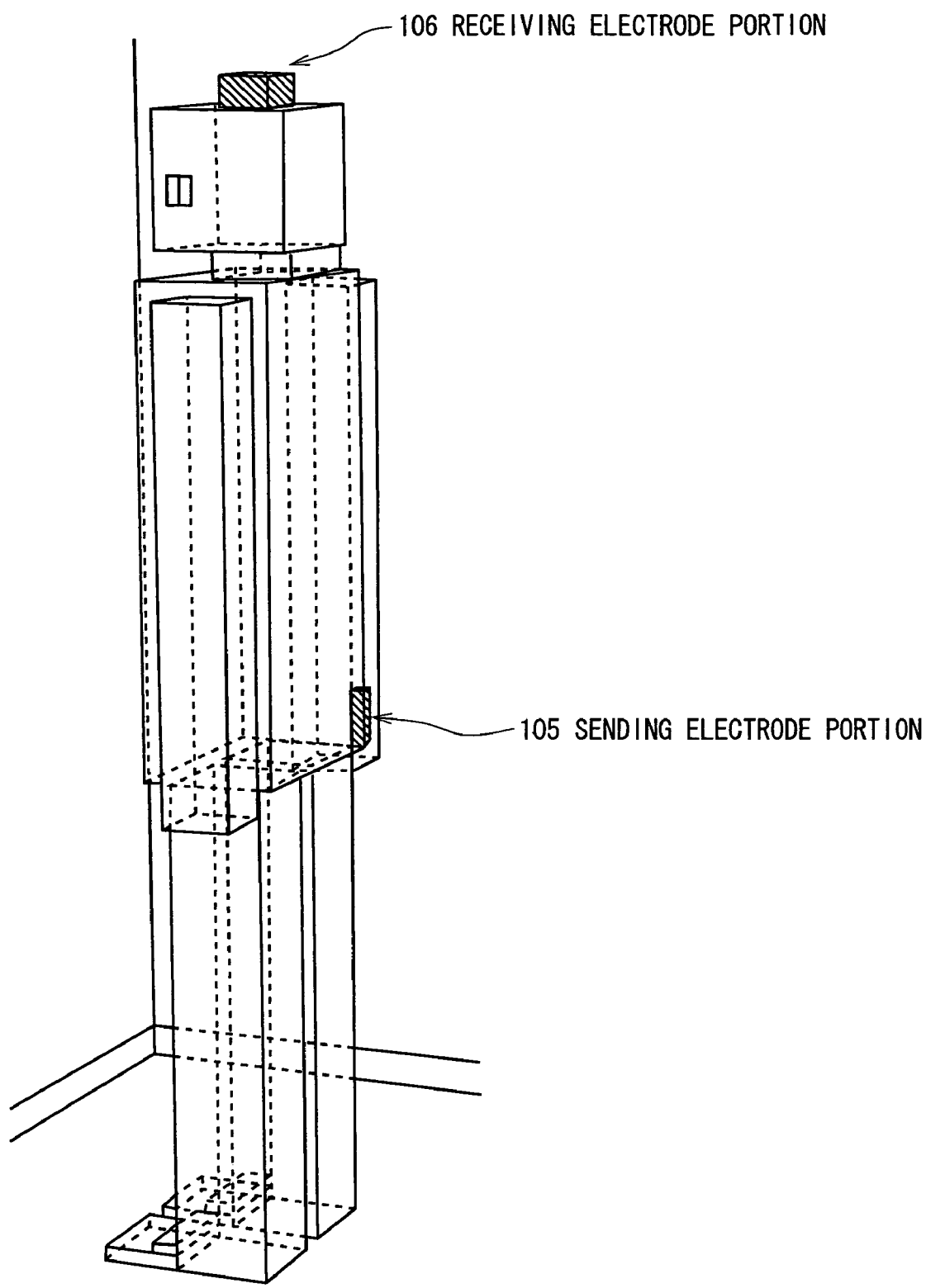
FIG. 23 is a schematic diagram showing a human body model example for performing simulation using the FDTD method.

Specifically, the simulation was performed in the condition that the sending electrode portion 105 is arranged at a position corresponding to a hip pocket of a human body model and the receiving electrode portion 106 is arranged at a position corresponding to the top of the head, as shown in FIG. 23, under the assumption that voltage of 1 [V] is applied at 100 [MHz] between the electrodes of the sending electrode portion 105, and under various other conditions. The results of the simulation are shown in FIGS. 24 to 27.

Figure 24:
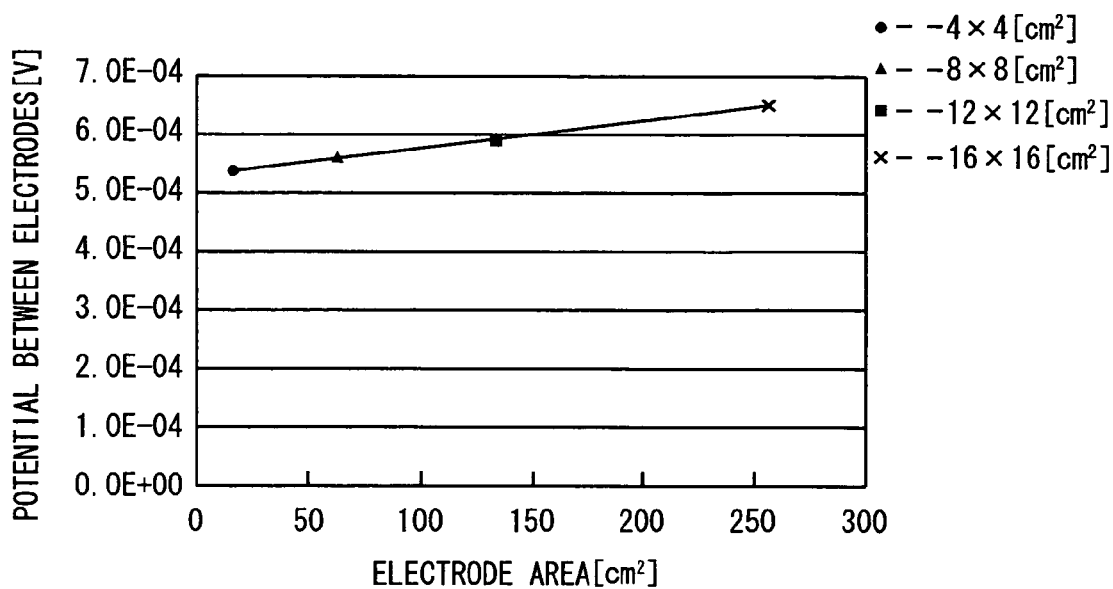
FIG. 24 is a schematic diagram showing the relation between the electrode area and the potential between electrodes on the receiving side.

FIG. 24 shows the relation between the electrode area of the receiving electrode portion 106 and the potential between electrodes of the receiving electrode portion 106. In this case, the electrode area of the sending electrode portion 105 was fixed at 8×4 [$cm^2$]; the distance between electrodes of the sending electrode portion 105 at 2 [cm]; and the distance between electrodes of the receiving electrode portion 106 at 1 [cm].

As apparent from FIG. 24, even if the electrode area of the receiving electrode portion 106 changes, the potential between the electrodes is almost constant. This means that it is possible to secure stabilization of communication even if, in designing a transmitter and a receiver, the electrode area of the receiving electrode portion 106 on the receiver side is reduced.

Figure 25:
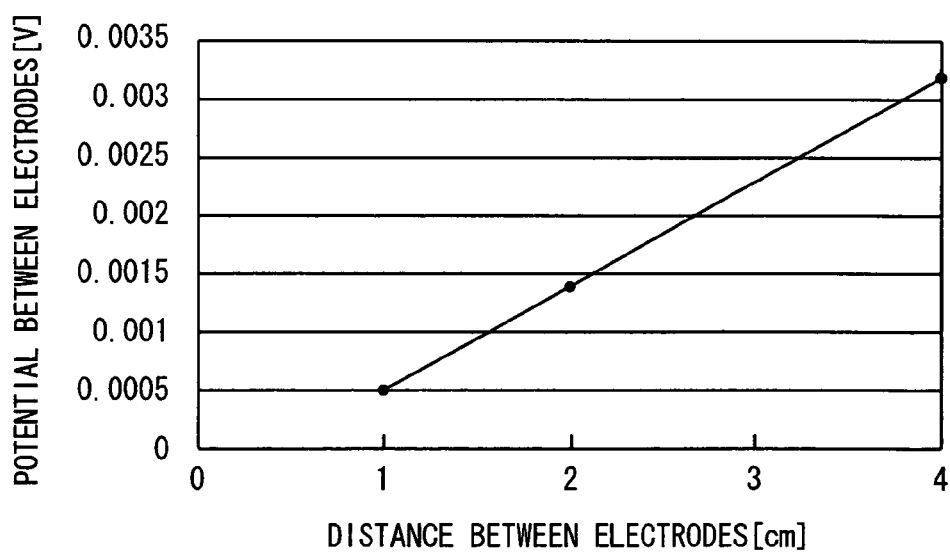
FIG. 25 is a schematic diagram showing the-relation between the distance between electrodes and the potential between electrodes on the receiving side.

FIG. 25 shows the distance between electrodes of the receiving electrode portion 106 and the potential between electrodes of the receiving electrode portion 106. The electrode area of the sending electrode portion 105 was fixed at 8×4 [$cm^2$], the distance between electrodes of the sending electrode portion 105 at 2 [cm]; and the electrode area of the receiving electrode portion 106 at 4×4 [cm²].

As apparent from FIG. 25, if the distance between electrodes of the receiving electrode portion 106 is denoted by $d_R$ [m] and the potential between electrodes of the receiving electrode portion 106 is denoted by $V_R$ [V], the distance between electrode $d_R$ and the potential between electrodes $V_R$ are in the relation represented by $V_R(d_R)=0.00088d_4-0.00034$. Since the potential between electrodes $V_R$ is less affected by the constant term 0.00034 but is greatly affected by change of the distance between electrode $d_R$, the constant term can be omitted. As a result, the distance between electrode $d_R$ and the potential between electrodes $V_R$ can be in the relation represented by the following equation.

$$V_R(d_R)=0.00088d_R \quad (15)$$

Figure 26:
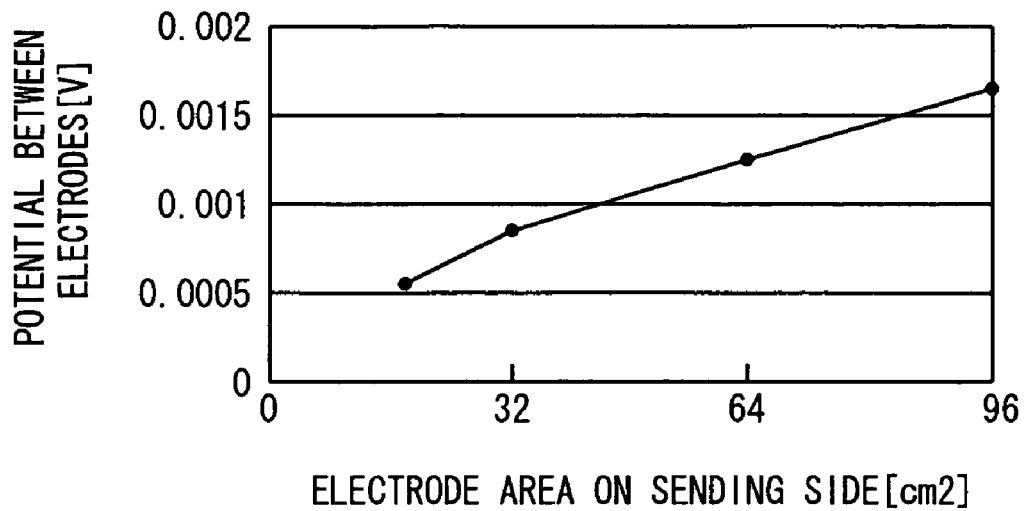
FIG. 26 is a schematic diagram showing the relation between the electrode area on the sending side and the potential between electrodes on the receiving side.

Furthermore, FIG. 26 shows the relation between the electrode area of the sending electrode portion 105 and the potential between electrodes of the receiving electrode portion 106. In this case, the distance between electrodes of the sending electrode portion 105 was fixed at 2 [cm]; the electrode area of the receiving electrode portion 106 at 4×4 [cm²]; and the distance between electrodes of the receiving electrode portion 106 at 1 [cm].

As apparent from FIG. 26, the relation between the potential between electrodes of the receiving electrode portion 106 and the electrode area of the sending electrode portion 105 is approximately a proportional relation.

Figure 27:
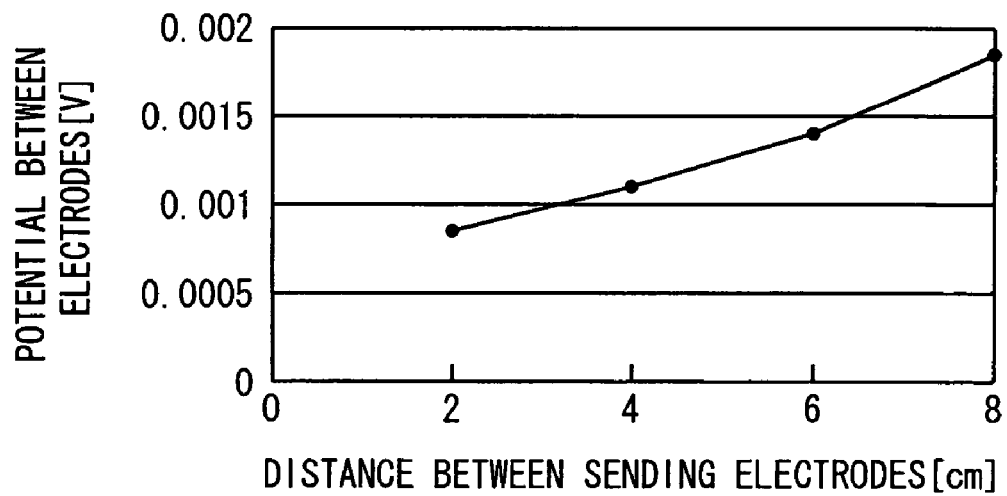
FIG. 27 is a schematic diagram showing the relation between the distance between electrodes on the sending side and the potential between electrodes on the receiving side.

As apparent from FIG. 27, the relation between the potential between electrodes of the receiving electrode portion 106 and the distance between electrodes of the sending electrode portion 105 is approximately a proportional relation.

FIG. 27 shows the relation between the distance between electrodes of the sending electrode portion 105 and the potential between electrodes of the receiving electrode portion 106. In this case, the electrode area of the sending electrode portion 105 was fixed at 8×4 [cm²]; the electrode area of the receiving electrode portion 106 at 4×4 [cm²]; and the distance between electrodes of the receiving electrode portion 106 at 1 [cm].

As apparent from FIG. 27, the potential between electrodes of the receiving electrode portion 106 is in proportion to the distance between electrodes of the sending electrode portion 105.

From the above simulation results (FIGS. 24 to 27), if the distance between electrodes of the receiving electrode portion 106 is denoted by $d_R$ [m], the electrode area of the sending electrode portion 105 by $A_S$ [m²], the distance between electrodes of the sending electrode portion 105 by $d_S$ [m], and the potential (hereinafter referred to as applied potential) to be applied between the sending electrode 105a and the reference electrode 105b of the sending electrode portion 105 is denoted by $V_S$ [V], then the potential between electrodes $V_R$ [V] of the receiving electrode portion 106 is shown by the following formula:

$$V_R \alpha \times V_s \times A_s \times d_s \times d_R \quad (16)$$

The reason why the electrode area of the receiving electrode portion 106 is not considered in the above formula (16) is that the potential between electrodes $V_R$ [V] of the receiving electrode portion 106 does not depend on the electrode area, as shown in FIG. 24.

In the above formula (16), the constant $\alpha$ is the potential gradient between the electrodes of the receiving electrode portion 106 relative to the potential applied to the sending electrode portion 105 and is a constant depending on the setting parameters (b) and (c) selected in consideration of the designing conditions (the constant is hereinafter referred to as a parameter dependent constant).

The potential $V_S$ applied to the sending electrode portion 105 depends on the frequency f and, therefore, is actually represented by the following formula.

$$V_R(f)=\alpha \times V_S(f) \times A_S \times d_S \times d_R$$

As described above, the potential between electrodes of the receiving electrode portion 106 can be formulated as a relative potential according to the designing parameter (b), relative to the potential applied to the sending electrode portion 105, as shown by the formula (17).

(3-4-3) Determination of a Parameter Depending Constant

Accordingly, the parameter depending constant a can be determined by performing such a simulation as shown in FIG. 23 with a predetermined electric field simulator only if the setting parameters (b) and (c) are selected.

That is, each of a human body model and the contents of the setting parameters (b) and (c) is defined in an electromagnetic field simulator, and then, by causing excitation between the electrodes 105a and 105b of the sending electrode portion 105 by a signal with a certain frequency and a predetermined amplitude, the potential between electrodes $V_R$ (f) generated at the receiving electrode portion 106 is calculated through simulation.

Here, since all the elements of the formula (17) are known except for the parameter depending constant $\alpha$, the parameter depending constant $\alpha$ can be determined by substituting the known values into the formula (17).

For example, in the case where, as the various conditions for the simulation in FIGS. 24 27, the electrode area $A_S$ of the sending electrode portion 105 is assumed to be 8×4 [cm²], the distance between electrodes $d_S$ of the sending electrode portion 105 is assumed to be 2 [cm], the distance between electrodes $d_R$ of the receiving electrode portion 106 is assumed to be 2 [cm], the potential $V_S$ (f) to be applied to the sending electrode portion 105 is assumed to be 1 [V] with a single frequency, the sending electrode portion 105 is assumed to be positioned at a hip pocket, and the receiving electrode portion 106 is assumed to be positioned at the head top of a human body, the potential between electrodes $V_R$ (f) generated at the receiving electrode portion 106 is 0.00088 [V] as shown in the simulation result in FIG. 25 and in the formula (15). Then, by substituting the corresponding values into the formula (17), $0.00088=\alpha \times 1 \times 0.0032 \times 0.02 \times 0.01$ is obtained, and consequently the parameter depending constant $\alpha$ can be determined to be 1375. consequently the parameter depending constant a can be determined to be 781.25.

As described above, the parameter depending constant a based on the selected setting parameters (b) and (c) can be determined from the electric field simulator and the formula (17). However, there is a certain correspondence relationship between the frequency and the distance between the sending and receiving sides, and therefore, the setting parameter (c) is determined to some extent if once the originating frequency of the setting parameters (a) is determined.

(3-4-4) Maximum Potential Applicable to a Sending Electrode Portion

When designing a transmitter and a receiver with the setting parameters (a) to (c), the setting parameter (d) (the potential to be supplied to the sending electrode portion 105) is determined such that the strength of the induction field component of the electric field generated from the sending electrode portion 105 is below the noise floor. The maximum potential applicable to the sending electrode portion 105 will be described here.

The electric field strength E at the position r in the neighborhood of an electric field source (the sending electrode portion 105) in free space at time t can be represented as the following formula, by rearranging the formula (2) under the assumption of "cos ωt=1", at which the electric strength E is the maximum, and under the assumption of θ=π/2 for simplification of the discussion:

$$E = E_0 = \frac{ql}{4\pi\varepsilon r^3} \cdot (1 + jkr + (jkr)^2) \cdot \exp(-jkr) \quad (18)$$

The received power p [W] received by an antenna with an aperture area K [m$^2$] is represented by the following formula:

$$p = \frac{SK}{4\pi} \quad (19)$$

where the received power density is denoted by S [W/m$^2$]. The received power density S [W/m$^2$] in the relation with the received electric strength E is represented by the following formula:

$$S = \frac{E^2}{120\pi} \quad (20)$$

Based on the induction filed component of the electric field:

$$p = \frac{SK}{4\pi} = \frac{E^2 K}{480\pi^2}$$
$$= 1000 \cdot \frac{E^2 K}{480\pi^2} [mW] \quad (21)$$

the component $S_2$ for the induction field of the power density is represented by the following formula:

Accordingly, the induction field component p of the received power is as follows:

$$1000 \cdot \frac{\left(\frac{ql_{max}}{4\pi\varepsilon r^3} \cdot |jkr \cdot \exp(-jkr)|\right)^2 \cdot K}{480\pi^2} = 10^{\frac{nf-10}{10}} \quad (23)$$

The formulas (20) and (21) are substituted for the $E_2$ and $H_9$ in the formula (23), respectively, and the product ql of the charge q of a microdipole and the distance l between two charges of the microdipole is obtained so that the induction field component p becomes smaller than the noise floor nf [dBm] by 10 [dB] at a distance of r from the electric field source (microdipole). Since $$1000 \cdot \frac{E^2 K}{480\pi^2} = 1000 \cdot \frac{\left(\frac{ql}{4\pi\varepsilon r^3} \cdot |jkr \cdot \exp(-jkr)|\right)^2 \cdot K}{480\pi^2} < 10^{\frac{nf-10}{10}} \quad (22)$$

by rearranging the following equation:

the maximum value of the product ql (hereinafter referred to as the maximum product) $ql_{max}$ is obtained.

$$ql_{max} = \sqrt{10^{\frac{nf-10}{10}} \cdot \frac{480\pi^2}{1000 \cdot K} \cdot \frac{4\pi\varepsilon r^3}{|jkr \cdot \exp(-jkr)|}} \quad (24)$$

In this formula (24), a function Re is used to represent the real part of the complex number.

The noise floor nf is defined by the following formula:

$$nf = 174[dBm/Hz] + NF + 10 \log B [dBm] \quad (25)$$

where NF is a noise index and B [Hz] is a communication band.

Practically, for example, in the case where the frequency f is 4 [MHz], the noise index NF is 10 [dB], the communication band B is 100 [kHz], the aperture area K of the receiving electrode portion 106 is 0.03 [m$^2$], and θ=π/2, it is apparent from the formula (24) that the output of an induction field at a distance of 0.05 [m] from the sending electrode portion 105 can be below the noise floor nf(=−174+10+10 log (1000000)=114 [dBm]) if the maximum product $ql_{max}$ is $ql_{max}$=6.28×10$^{-15}$. However, actually, if the product ql satisfies "ql<$ql_{max}$", then the induction field component at a neighbor position r at a distance of 0.05 [m] from the sending electrode portion 105 can be below the noise floor nf.

Here, confirmation will be now made on the relation of the communication distance with the electric field strength of the composite electric field comprising the quasi-electrostatic field, the induction field and the radiation field, and with the electric field strength only of the induction field.

That is, by substituting θ=π/2 and $ql_{max}$=6.28×10$^{-15}$ into the formula (18), the electric field strength E ($E_\theta$) of the composite electric field is represented by the following formula:

$$E = \quad (26)$$

$$E_\theta = \frac{ql_{max}}{4\pi\varepsilon r^3}(1 + jkr + (jkr)^2) \cdot \exp(-jkr)$$
$$= \frac{1.5 \times 10^{-16}}{4\pi\varepsilon r^3}\left(1 + j\frac{2\pi f}{c}r + \left(j\frac{2\pi f}{c}r\right)^2\right) \cdot \exp(-jkr)$$

Figure 28:
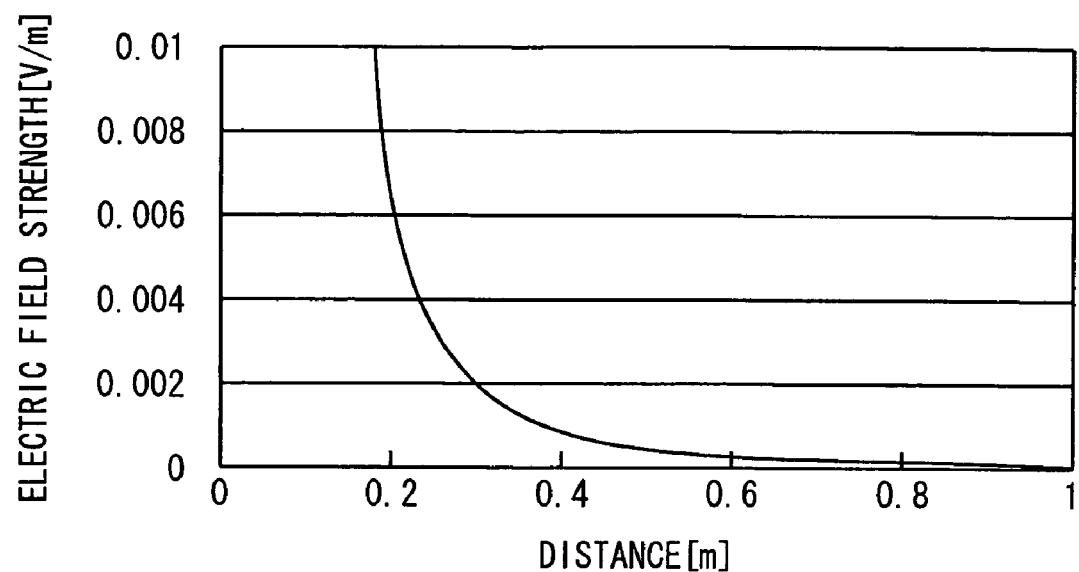
FIG. 28 is a schematic diagram showing the relation between the electric strength of a composite electric field and the distance from the electric field source.

By substituting to the formula (26) the permittivity of vacuum electric constant ε=8.85e-12, the frequency f=4e6, and the wavelength k=2πf/c (c: light velocity), the electric field strength E of the composite electric field and the neighbor distance r from the electric field source can be plotted in the relation shown in FIG. 28.

Figure 29:
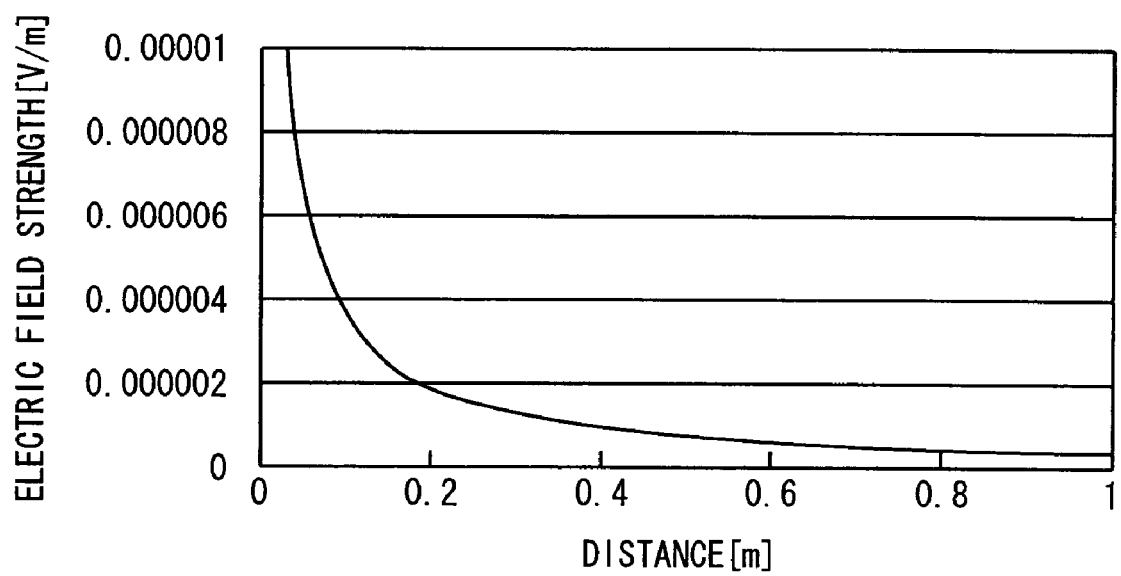
FIG. 29 is a schematic diagram showing the relation between the electric field strength of the induction field and the distance from the electric field source.

The electric field strength E of the induction field component, defined by the following formula:

$$E = \frac{ql_{max}}{4\pi\varepsilon r^3}(jkr) \cdot \exp(-jkr) \quad (27)$$

and the neighbor distance r from the electric field source can be plotted in the relation shown in FIG. 29.

As apparent from comparison of FIG. 28 and FIG. 29, it can be confirmed that the strength of the induction field is sufficiently smaller in comparison with the quasi-electrostatic field at the position r in the neighborhood of the electric field source (the sending electrode portion 105). Since the strength of the radiation field not shown in FIGS. 28 and 29 is smaller than that of the induction field at the neighbor position r, it is apparently smaller than the strength of the quasi-electrostatic field.

If the frequency f, the noise index NF, the communication band B, a distance r between the sending electrode portion 105 and the neighbor position, and the aperture area K of the virtual antenna for evaluating power at the neighbor position are specifically determined, the maximum product $ql_{max}$ of the charge q and the distance l from the charge of the microdipole and can be determined from the formula (24).

The maximum product $ql_{max}$ corresponds to the maximum potential applicable to the sending electrode-portion 105. Therefore, if the applied potential $V_S$ ($A_S$, $d_S$, f) to be applied to the sending electrode portion 105 can be determined using an electric field simulator such that the electric field with an electrode area $A_S$ selected as the setting parameter (b) and a distance between electrodes $d_S$, generated from the sending electrode portion 105, substantially corresponds to the curve in FIG. 28, which obtained as a result of plotting based on the formula (26), then the strength of the induction field can be below the noise floor nf at a limit position $r_{neighbor}$ (=neighbor distance r) in the communication range with the sending electrode portion 105 as the center thereof.

For example, when a sending electrode portion 105 with an electrode area $A_S$ of 4×4 [cm²] and a distance between electrodes $d_S$ of 4 [cm] was arranged in free space, and a potential of 1 [V] was applied to the sending electrode portion 105 with a single frequency $f_0$, the electric field generated from the sending electrode portion 105 multiplied by 0.084 almost corresponded to the curve of FIG. 28.

This means that, if a potential $V_S$ of 0.084 [V](0.04×0.04, 0.04, $f_0$) is applied to the sending electrode portion 105, the strength of the induction field at a limit position $r_{neighbor}$ in the communication range with the sending electrode portion 105 as the center thereof is below the noise floor nf.

From this, the maximum potential (hereinafter referred to as maximum applicable potential) $AV_{Smax}$ ($A_S$, $d_S$, f) which can be applied to the sending electrode portion 105 and which corresponds to the maximum $ql_{max}$ (f) depending on the frequency f is represented by the following formula:

$$AV_{Smax}(A_S, d_S, f) = \sqrt{10^{\frac{-174+10+10\log(B)-10}{10}} \cdot \frac{480\pi^2}{1000 \cdot K}} \cdot \frac{\frac{4\pi\varepsilon \cdot r_{neighbour}^3}{\left|\left(j\frac{2\pi f}{c}r_{neighbour}\right) \cdot \exp\left(-j\frac{2\pi f}{c}r_{neighbour}\right)\right|} \times \frac{V_S(A_S, d_S, f_0)}{ql_{max}(f_0)}} \quad (28)$$

where the single frequency used in the simulation by the electric field simulator is denoted by $f_0$ and the potential to be obtained which has been obtained by the simulation is denoted by $V_S$ ($A_S$, $d_S$, $f_0$).

As an example, when the conditions of the simulation results (the potential $V_S$ (0.04×0.04, 0.04, 4) applied to the sending electrode portion 105 with an electrode area $A_S$ of 4×4 [cm²] and a distance between electrodes $d_S$ of 4 [cm] was 0.084 [V]) are added to the conditions in the case where the maximum product $ql_{max}$ is assumed to be 6.28×10⁻¹⁵ from the formula (24) (the single frequency $F_0$ is 4 [MHz], the noise index NF is 10 [dB], the communication band B is 100 [kHz], the aperture area K of the antenna used for evaluating power at a distance of 0.05 [m] is 0.03 [m²] and θ=π/2), by substituting the values into the corresponding terms, in the formula (28), the maximum applicable potential is represented by the following formula:

$$AV_{Smax}(0.04 \times 0.04, 0.04, f) = \sqrt{10^{\frac{-174+10\log(100000)}{10}} \cdot \frac{480\pi^2}{1000 \cdot 0.03^2}} \cdot \frac{\frac{4\pi\varepsilon \cdot 0.05^3}{\left|j\frac{2\pi f}{c}0.05 \cdot \exp\left(-j\frac{2\pi f}{c}0.05\right)\right|} \times \frac{0.002}{ql(4 \times 10^6)}} \quad (29)$$

Figure 30:
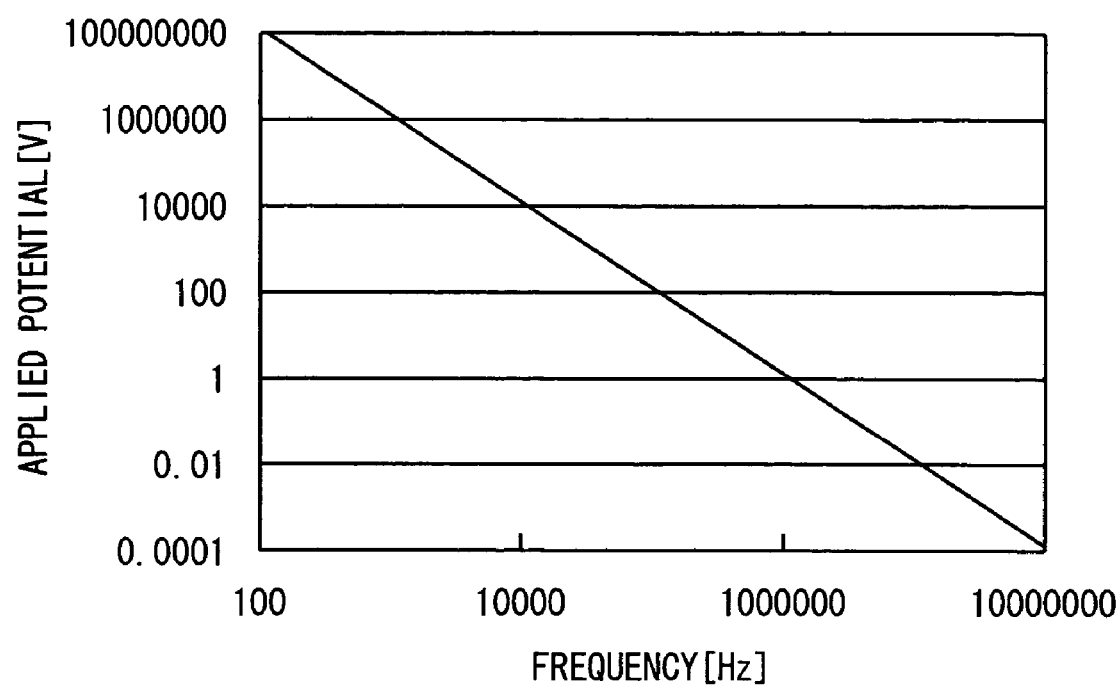
FIG. 30 is a schematic diagram showing the relation between applied potential and frequency.

FIG. 30 shows the relation between the frequency f and the maximum applicable potential $AV_{Smax}$ (0.04×0.04, 0.04, f) based on the above formula (29). As apparent from FIG. 30, the electric field strength of the induction field at a distance of 5 [cm] from the electric field source (the sending electrode portion 105) can be below the noise floor at any frequency f.

As described above, the maximum applicable potential $AV_{Smax}$ ($A_S$, $d_S$, f) according to the selected setting parameters (a) to (c) can be obtained from the electric field simulator and the formula (28).

(3-4-5) Selection of a Preamplifier

When a preamplifier 121 with a voltage noise of n [V/√Hz] is mounted on the headphone device 103, the preamplifier 121 is able to detect a signal with a potential n/√B [V] relative to a communication band B [Hz].

Accordingly, the preamplifier 121 can be selected to satisfy the following formula:

$$V_R(f) = \alpha \times V_S(f) \times A_S \times d_S \times d_R > n/\sqrt{B} \quad (30)$$

(3-4-6) Conclusion

Figure 31:
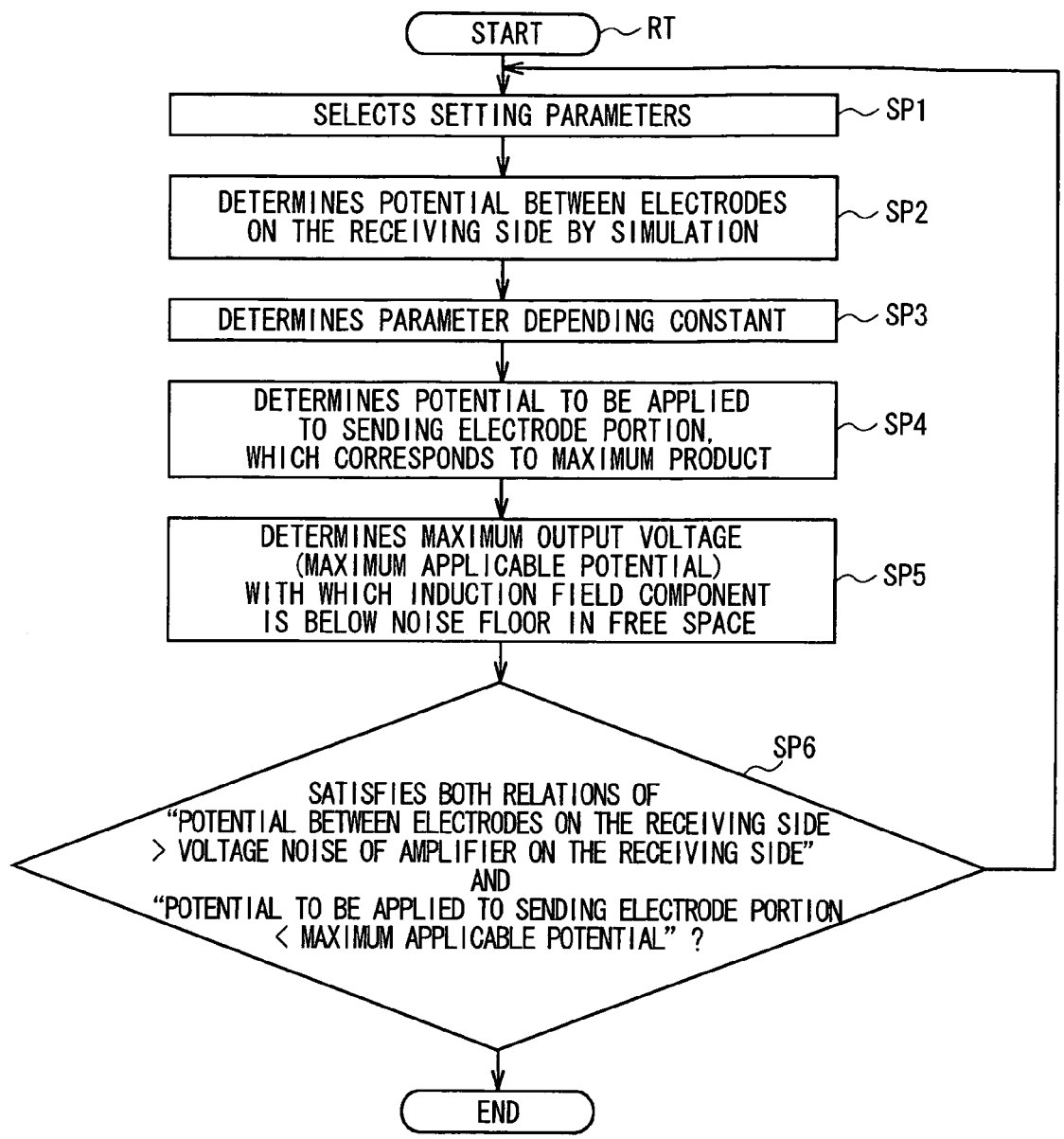
FIG. 31 is a flow chart showing a designing procedure.

To sum up the description above, designing for a transmitter and a receiver (the voice reproducer 102 and the headphone device 103) can be performed in accordance with the designing procedure RT in FIG. 31.

That is, selection of (a) the originating frequency f and the communication band B, (b) the electrode area As and the distance between electrodes $d_S$ of the sending electrode portion 105 and the distance between electrodes $d_R$ of the receiving electrode portion 106, (c) the positions of the sending electrode portion 105 and the receiving electrode portion 106 on a human body, and (d) the voltage noise n of the preamplifier 121 is performed first as preprocessing for designing (step SP1).

Then, a human body model as well as a sending electrode portion 105 and a receiving electrode portion 106 with the setting parameter (b) are defined in an electric field simulator; the sending electrode portion 105 and the receiving electrode portion 106 are arranged at positions on the human body model corresponding to the setting, parameters (c) on the human body; and the potential between electrodes $V_R(f)$ of the receiving electrode portion 106, shown when excitation is caused between the electrodes 105a and 105b of the sending electrode portion 105 by a predetermined applied potential $V_S(f)$ with an originating frequency f, is determined (step SP2).

After that, the defined terms are substituted with the corresponding portions of the formula (17) to determine the parameter depending constant a in the case of designing a transmitter and a receiver with the setting parameters (b) and (c) (step SP3).

Then, the aperture area K of the receiving electrode portion 106, the noise index NF and the limit position $r_{neighbor}$ in the communication range with the sending electrode portion 105 as the center thereof are determined, and the determined terms and the setting parameters (a) are substituted with the corresponding portions of the formula (24) to determine the maximum product $ql_{max}$.

The applied potential $V_S$ ($A_S$, $d_S$, $f_0$) to be applied to the sending electrode portion 105 is determined in the electric simulator such that the electric field generated from the sending electrode portion 105 with an electrode area $A_S$ and a distance between electrodes $d_S$ selected as the setting parameters (b) substantially corresponds to the electric field strength E ($E_\theta$) of a composite electric field obtained as a result of substituting the terms related to the determined maximum product $ql_{max}$ into the formula (18) (step SP4).

Then, by substituting the determined applied potential $V_S$ ($A_S$, $d_S$, $f_0$) into the formula (28), such maximum applicable potential $AV_{Smax}$ (AS, dS, f) that the strength of the induction field at the limit position $r_{neighbor}$ in the communication range with the sending electrode portion 105 as the center thereof is below the noise floor nf in free space (step SP5).

Finally, it is confirmed whether or not any applied potential $V_S(f)$ exists which is below the maximum applicable potential $AV_{Smax}$ ($A_S$, $d_S$, f) and which satisfies that the potential between electrodes $V_R(f)$ of the receiving electrode portion 106 is equal to or above the voltage noise n of the selected preamplifier 121, as the applied potential $V_S(f)$ to be supplied to the sending electrode portion 105 (step SP6).

If there is no such applied potential $V_S(f)$ as satisfies the conditions, all or a part of the setting parameters (a) to (d) are reviewed again, and the procedure from the steps SP2 to SP6 are repeated based on the reviewed and changed setting parameters.

On the contrary, if an applied potential $V_S(f)$ that satisfies the conditions exists, it means that the designing of a transmitter and a receiver was successful. The setting procedure then ends.

By performing the designing procedure RT shown in FIG. 31 as described above, the applied potential $V_S(f)$ to be applied to the sending electrode portion 105 according to arbitrarily selected setting parameters can be determined such that the strength of the induction field component within a predetermined range of an electric field generated from an electric field source is below a noise floor level.

When it is assumed that transmitters and receivers may be attached at multiple positions, it is possible to determine the application potential $V_S(f)$ to be applied according to the setting parameters for each of the transmitters and receivers at the positions by sequentially performing the procedure from the steps SP1 to SP6 for all the positions.

(3-5) Operation and Effects

In the above configuration, in the communication system 100, the sending electrode portion 105 is formed in a structure according to the reference frequency such that the strength of the induction field component of an electric field is below the noise floor specified according to the communication band.

Accordingly, in the communication system 100, energy required for communication is reduced by reduction of the induction field and radiation field components unnecessary for quasi-electrostatic field communication, and spatial resolution can be enhanced due to prevention of unnecessary propagation. Thus, stabilization of communication can be enhanced.

In addition, in the communication system 100, stabilization of communication can be enhanced more by limiting the voltage to be applied between sending electrodes according to the reference frequency.

According to the above configuration, the sending electrode portion, 105 is formed in a structure according to the reference frequency such that the strength of the induction field component of an electric field is to be below the noise floor specified according to the communication band. Accordingly, energy required for communication is reduced by reduction of the induction field and radiation field components unnecessary for quasi-electrostatic field communication, and spatial resolution can be enhanced due to prevention of unnecessary propagation. Thus, stabilization of communication can be enhanced and the degree of freedom in communication can be enhanced.

(3-6) Other Embodiments

In the second embodiment described above, description has been made on the case where an electric structure according to the reference frequency is selected based on the formula (16) such that the strength of the induction field component of an electric field is to be below the noise floor specified according to the communication band. The present invention, however, is not limited thereto, and the structure may be selected based on any formula other than the formula (16), such as a formula improved based on the formula (16).

Furthermore, in the second embodiment described above, description has been made on the case where a potential corresponding to a prespecified originating frequency (working frequency) is set and a signal with the set potential is generated and applied, as generation means for generating a signal to be applied to an electrode with the electrode structure according to the used frequency. The present invention, however, is not limited thereto, and it is also possible to hold multiple frequencies and potentials corresponding to frequencies in a table, refer to the table to determine a potential corresponding to the frequency to be used, and sequentially generate signals with the determined potential by switching them at a predetermined timing to apply them.

In this case, since communication can be performed with the headphone device 103 using multiple frequencies, it is possible to enhance communication efficiency while maintaining stabilization of communication.

Furthermore, in the second embodiment described above, description has been made, as for the positions of a transmitter and a receiver, on the case where the voice reproducer 102 is positioned at a hip pocket of clothes over a human body and the headphone device 103 is positioned at the head top of the human body. The present invention, however, is not limited thereto, and the transmitter and the receiver (the voice reproducer 102 and the headphone device 103) may be arranged at various other positions.

Furthermore, as for combination of a transmitter and a receiver, various other combinations of a transmitter and a receiver may be applied, including the case of communication between a mobile telephone and a personal computer. In this case, a set of a sending electrode portion 105 and a receiving electrode portion 106 is mounted on both of the transmitter and the receiver.

Furthermore, in this case, information to be sent and received may be information other than voice; the number of human bodies via which the information passes may be any number, and organisms such as mammals, reptiles, plants, even a predetermined conductive material and various other targets may be applied instead of a human body.

INDUSTRIAL APPLICABILITY

The present invention can be applied to the case where near field communication is performed utilizing potential difference between electrodes of a transmitter and a receiver, and particularly to the case where information is sent and received via a human body.

The invention claimed is:

1. A communication system comprising:
a first communication device for electrifying an electrification target having electrification properties by generating a quasi-electrostatic field modulated according to information to be sent; and
a second communication device for detecting change in electrification condition of the electrification target and demodulating the information based on the change,
wherein the electrification target is a human body, and
wherein the modulation means performs the modulation according to information to be sent so that a relation of $r=\lambda/2\pi$ is satisfied where a longest distance between the electric field generation electrode and a detection electrode for detecting the quasi-electrostatic field is taken to r and a wavelength of the modulated signal to be output to the electric field generation electrode is taken to $\lambda$.

2. The communication system according to claim 1, wherein each of the first communication device and the second communication device is of a portable type, and the first communication device and the second communication device are provided in a neighborhood of different human bodies.

3. The communication system according to claim 1, wherein the first communication device is of a portable type and provided in a neighborhood of the human body; and
the second communication device is provided on or in a neighborhood of a predetermined control target.

4. A communication device comprising:
an electric field generation electrode for generating an electric field; and
modulation means for performing modulation according to information to be sent so that an electrification target is electrified by a quasi-electrostatic field out of the electric field generated from the electric field generation electrode, and outputting a modulated signal resulted from the modulation, to the electric field generation electrode,
wherein the electrification target is a human body, and
wherein the modulation means performs the modulation according to information to be sent so that a relation of $r=\lambda/2\pi$ is satisfied where a longest distance between the electric field generation electrode and a detection electrode for detecting the quasi-electrostatic field is taken to r and a wavelength of the modulated signal to be output to the electric field generation electrode is taken to $\lambda$.

5. The communication device according to claim 4, wherein the modulation means performs the modulation according to information to be sent so that the human body is electrified by the quasi-electrostatic field as an antenna.

6. The communication device according to claim 4, wherein the communication device is of a portable type and is provided in a neighborhood of the human body.

7. The communication device according to claim 4, wherein the modulation means outputs the modulated signal in a condition where at least one of electric power and electric charge is limited.

8. The communication device according to claim 4, wherein the modulation means performs the modulation according to information to be sent so that the quasi-electrostatic field generated from the electric field generation electrode is dominant, based on a distance between the electric field generation electrode and a detection electrode for detecting the quasi-electrostatic field and a wavelength of the modulated signal to be output to the electric field generation electrode.

9. The communication device according to claim 4, wherein
the electric field generation electrode forms an electric route to an electric field generation electrode of a communication counterpart via the electrification target electrified by the communication counterpart, and comprises a storage means for storing a signal occurring in the route, as own starting power.

10. The communication device according to claim 4, wherein:
the electric field generation electrode is a parallel plane electrode; and
in the parallel plane electrode, an electrode area and a distance between electrodes are determined so that a strength induction field component of an electric field at a prescribed position in a neighborhood of the parallel plane electrode is below a noise floor specified according to a communication band, when electric potential of a reference frequency is supplied.

11. The communication device according to claim 4, wherein
the electric field generation electrode is a parallel plane electrode; and
in the parallel plane electrode, an electrode area and a distance between electrodes are determined so that a strength induction field component of an electric field at a prescribed position in a neighborhood of the parallel plane electrode is below a noise floor specified according to a communication band and is larger than a noise generated in the detection means of a communication counterpart for detecting the electric field, when electric potential of a reference frequency is supplied.

12. The communication device according to claim 7, wherein,
in the parallel plane electrode, in a case where an electrode area is taken to $A_S$ [m$^2$], a distance between electrodes is taken to $d_S$ [m], potential between electrodes is taken to $V_S$ [V], potential between electrodes and a distance between electrodes of a parallel plane electrode in a communication counterpart is taken to $V_R$ [V] and $d_R$ [m], and a constant depending on the distance between electrodes $d_R$, the electrode area $A_S$, and the distance between electrodes $d_S$ is taken to $\alpha$, the electrode area $A_S$ and the distance between electrodes $d_S$ are determined so that a following formula $V_R = \alpha \times V_S \times A_S \times d_S \times d_R$ is satisfied, when the distance between electrodes $d_R$ is fixed and potential between electrodes $V_S$ of a reference frequency is supplied.

13. The communication device according to claim 9, wherein:
the electrification target is a human body; and
the communication device comprises:
a power supply electrode for generating the quasi-electrostatic field for power supply to a communication counterpart;
a detection electrode for detecting an electrification condition of the human body according to walking of the human body; and power supply means for supplying a signal for power supply to the power supply electrode only while the detection electrode detects the electrification condition.

14. A communication device comprising:
detection means for detecting an electrification condition of an electrification target electrified by a quasi-electrostatic field out of an electric field based on a modulated signal obtained through modulation according to information to be sent; and
demodulation means for modulating the information based on change in the electrification condition detected by the detection means,
wherein the electrification target is a human body, and
wherein the detection means detects an electrification condition of an electrification target electrified by the quasi-electrostatic field based on a modulated signal resulted from modulation according to information to be sent so that a relation of $r=\lambda/2\pi$ is satisfied where a longest distance between the electric field generation electrode and a detection electrode for detecting the quasi-electrostatic field is taken to r and a wavelength of the modulated signal to be output to the electric field generation electrode is taken to $\lambda$.

15. The communication device according to claim 14, wherein the detection means detects an electrification condition of a human body electrified by the quasi-electrostatic field as an antenna.

16. The communication device according to claim 14, wherein the communication device is of a portable type and provided in a neighborhood of the human body.

17. The communication device according to claim 14, wherein the communication device is provided on or in a neighborhood of a prescribed control target.

18. The communication device according to claim 14, wherein the detection means detects an electrification condition of an electrification target electrified by the quasi-electrostatic field based on a modulated signal resulted from modulation according to information to be sent so that the quasi-electrostatic field is dominant based on a distance between the electric field generation electrode and a detection electrode for detecting the quasi-electrostatic static field and a wavelength of the modulated signal to be output to the electric field generation electrode.

19. The communication device according to claim 14, comprising
leakage preventing means for preventing electrical leakage from a route from the detection means to the demodulation means.

20. The communication device according to claim 19, wherein the leakage preventing means causes an electrostatic capacity from the detection means to the ground via the demodulation means to be larger than an electrostatic capacity between the detection means and the ground.

21. The communication device according to claim 19, wherein:
the detection means has a detection electrode for detecting the electrification condition and conversion means for converting the electrification condition detected by the detection electrode into an electric signal; and
the leakage preventing means comprises a case for physical separation into the detection electrode and the conversion means.

22. The communication device according to claim 19, wherein the leakage preventing means grounds only the demodulation means out of the route from the detection means to the demodulation means.

23. The communication device according to claim 14, wherein:
the electrification target is a moving entity; and
the communication device comprises:
a power supply electrode for generating the quasi-electrostatic field for power supply to a communication counterpart; and
coupling preventing means for preventing electrical coupling between the electrification target and the ground, the coupling preventing means being provided on a passage through which the electrification target passes.

24. The communication device according to claim 23, wherein the coupling preventing means is formed with a floor surface provided at a prescribed distance from the ground.

25. The communication device according to claim 23, wherein the coupling preventing means is formed with a low-dielectric-constant member covered over the passage and connected to the ground.

26. The communication device according to claim 14, wherein:
the electrification target is a human body; and
the communication device comprises:
a power supply electrode for generating the quasi-electrostatic field for power supply to a communication counterpart; and
a detection electrode for detecting an electrification condition caused in the human body according to walking of the human body, wherein
the power supply electrode and the detection electrode comprise the same electrodes.

27. The communication device according to claim 14, comprising:
a power supply electrode for generating the quasi-electrostatic field for power supply to a communication counterpart; and
power supply means for supplying a signal for the power supply to the power supply electrode, wherein
the power supply means also uses the signal for the power supply as a carrier signal to be sent to the communicating party.

28. The communication device according to claim 14, wherein:
the detection means has a detection electrode comprising a parallel plane electrode for detecting the electrification condition; and
in the parallel plane electrode, a distance between electrodes is determined, independently from an electrode area, so that a strength induction field component of an electric field at a prescribed position in a neighborhood of the parallel plane electrode is below a noise floor specified according to a communication band, when potential of a reference frequency is supplied to a parallel plane electrode of a communication counterpart existing at a prescribed position.

29. The communication device according to claim 14, wherein:
the detection means has a detection electrode comprising a parallel plane electrode for detecting the electrification condition; and
in the parallel plane electrode, a distance between electrodes is determined, independently from an electrode area so that a strength induction field of an electric field at a prescribed position in a neighborhood of the parallel plane electrode is below a noise floor specified according to a communication band and is larger than a noise generated in the detection means, when potential of a reference frequency is supplied to a parallel plane electrode of a communication counterpart existing at a prescribed position.

30. The communication device according to claim 14, wherein:

the detection means has a detection electrode comprising a parallel plane electrode for detecting the electrification condition; and in the parallel plane electrode, in a case where potential between electrodes $V_R$ [V], a distance between electrodes $d_R$ [m], an electrode area of a parallel plane electrode of a communication counterpart is taken to $A_S$ [m²], a distance between electrodes is taken to $d_S$ [ms], potential between electrodes is taken to $V_S$ [V], and a constant depending on the distance between electrodes $d_R$, the electrode area $A_S$, and the distance between electrodes $d_S$ is taken to $\alpha$, the distance between electrodes $d_R$ is determined so that a following equation $V_R = \alpha \times V_S \times A_S \times d_S \times d_R$ is satisfied, when the distance between electrodes $d_R$ is fixed and potential between electrodes $V_S$ of a reference frequency is supplied.

31. An electrode manufacturing method of an electrode to be used in communicating a quasi-electrostatic field as an information communication medium, wherein a first step of selecting an originating frequency and a communication band for communication, a distance between electrodes and an electrode area of a sender parallel plane electrode to be used as a sender electrode, and a distance between electrodes of a receiver parallel plane electrode to be used as a receiver electrode;

a second step of determining a communication limit position between the sender parallel plane electrode and the receiver parallel plane electrode based on a matter selected in the first step; and a third step of determining whether potential exists where a strength induction field component of an electric field at the communication limit position determined in the second step is below a noise floor specified according to the communication band, when potential of the originating frequency is supplied to the sender parallel plane electrode.

32. The electrode manufacturing method according to claim 31, wherein:

in the first step, a preamplifier to be connected to the receiver parallel plane electrode is selected in addition to the originating frequency and the communication band, the distance between electrodes and the electrode area of the sender parallel plane electrode, and the distance between electrodes of the receiver parallel plane electrode; and the electrode manufacturing method further comprises a fourth step of determining whether potential between electrodes caused in the receiver parallel plane electrode is larger than a voltage noise of the preamplifier when such determination result is obtained in the third step that the potential below the noise floor exists.

* * * * *